United States Patent [19]

Rogart

[11] Patent Number: 5,380,836
[45] Date of Patent: Jan. 10, 1995

[54] NUCLEIC ACID ENCODING SODIUM CHANNEL PROTEIN

[75] Inventor: Richard B. Rogart, Chicago, Ill.

[73] Assignee: Arch Development Corporation, Chicago, Ill.

[21] Appl. No.: 768,107

[22] Filed: Sep. 30, 1991

Related U.S. Application Data

[63] Continuation of Ser. No. 331,330, Feb. 13, 1989, abandoned.

[51] Int. Cl.$^6$ .................. C07H 21/02; C07H 21/04; C12Q 1/68; C12N 5/10
[52] U.S. Cl. ......................................... 536/23.5; 435/6; 435/240.2; 435/240.4; 435/252.3; 435/320.1; 435/254.2; 935/77; 935/78
[58] Field of Search ................. 435/6, 240.2, 240.4, 435/252.3, 255, 320.1; 536/27, 23.5; 935/77, 78

[56] References Cited

FOREIGN PATENT DOCUMENTS 8304053 11/1983 WIPO .

OTHER PUBLICATIONS

Noda et al, Nature, vol. 320, pp. 188–192 (1986).
Agnew, W. S., Nature, 322:770–771 (1986).
Aldrich, R. W., et al., The Journal of Neuroscience, 7(2):418–431 (1987).
Auld, V. J., et al., Neuron, 1:449–461 (1988).
Barchi, R. L., ASPET Meeting Abstracts, (Aug. 1988).
Benton, W. D., et al., Science, 196:180–182 (1977).
Berent, S. L., et al., Bio Techniques, 3:208–220 (1985).
Bodkin, D. K., et al., Virology, 143:55–62 (1985).
Bonner, T. I., et al., Science, 237:527–532 (1987).
Casadei, J. M., et al., The Journal of Biological Chemistry, 261:4318–4323 (1986).
Catterall, W. A., Ann. Rev. Biochem., 55:953–985 (1986).
Catterall, W. A., et al., Molecular Pharmacology, 20:526–532 (1981).
Catterall, W. A., et al., Molecular Pharmacology, 20:533–542 (1981).
Chirgwin, J. M., et al., Biochemistry, 18:5294–5299 (1979).
Claudio, T., et al., Science, 238:1688–1694 (1987).
Cohen, C. J., et al., J. Gen. Physiol., 78:383–411 (1981).
Erlich, H. A., et al., Nature, 331:461–462 (1988).
Fozzard, H. A., et al., Circulation Research, 56:475–485 (1985).
Frelin, C., et al., Pflugers Archi, 402:121–128 (1984).
Goldin, A. L., et al., Proc. Nat'l. Acad. Sci. USA, 83:7503–7507 (1986).
Greenblatt, R. E., et al., FEBS, 193:125–134 (1985).
Gubler, U., et al., Gene, 25:263–269 (1983).
Guy, H. R., et al., Proc. Nat'l Acad. Sci. USA, 83:508–512 (1986).
Hanck, D. A., et al., Biophys. J., 53:534a (1988).
Hartshorne, R. P., et al., Proc. Nat'l Acad. Sci. USA, 78:4620–4624 (1981).
Imoto, K., et al., Nature, 324:670–672 (1986).
Kayano, T., et al., FEBS, 228:187–194 (1988).
Kent, R. B., et al., Science, 237:901–903 (1987).
Kohlhardt, M., et al., Membrane Biology, 103:283–291 (1988).
Lester, H. A., Science, 241:1057–1063 (1988).
Lopata, M. A., et al., Nucleic Acids Research, 12:5707–5717 (1984).

(List continued on next page.)

Primary Examiner—Mindy B. Fleisher
Attorney, Agent, or Firm—Marshall, O'Toole, Gerstein, Murray & Borun

[57] ABSTRACT

The present invention relates generally to sodium channel proteins and more particularly to mammalian cardiac sodium channel proteins, to DNA sequences encoding sodium channel proteins, to the polypeptide products of recombinant expression of these DNA sequences, to peptides whose sequences are based on amino acid sequences deduced from these DNA sequences, to antibodies specific for such proteins and peptides, and to procedures for detection and quantitation of such proteins and nucleic acids related thereto, as well as to procedures relating to the development of anti-arrhythmic and cardiotonic drugs.

8 Claims, 25 Drawing Sheets

OTHER PUBLICATIONS

Mackett, M., et al., Journal of Virology, 49:857–864 (1984).
Mandel, G., et al., Proc. Nat'l. Acad. Sci. USA, 85:924–928 (1988).
Merlie, J. P., et al., J. Membrane Biology, 91:1–10 (1986).
Messner, D. J., et al., The Journal of Biology Chemistry, 261:14882–14890 (1986).
Moczydlowski, E., et al., Proc. Nat'l. Acad. Sci. USA, 83:5321–5325 (1986).
Morikawa, Y., et al., Circulation Research, 57:354–361 (1985).
Noda, M., et al., Nature, 320:188–192 (1986).
Noda, M., et al., Nature, 322:826–828 (1986).
Noda, M., et al., Nature, 312:121–127 (1984).
Perbol, B., A Practical Guide to Molecular Cloning, NY, John Wiley, 751–779 (1988).
Price, E. M., ASPET Meeting Abstracts, (1988).
Redfern, P., et al., Acta Physiol. Scand., 82:70–78 (1971).
Renaud, J. F., et al., J. Biol. Chem., 258:8799–8805 (1983).
Ritchie, J. M., et al., J. Physiol., 269–354 (1977).
Ritchie, J. M., et al., Rev. Physiol. Biochem. Pharmacol., 79:1–50 (1977).
Rogart, R. B., et al., Ann. New York Acad. Sci., 479:402–430 (1986).
Rogart, R. B., et al., Brain Research, 329:314–318 (1985).
Rogart, R. B., et al., Proc. Nat'l. Acad. Sci. USA, 80:1106–1110 (1983).
Salkoff, L., et al., Science, 237:744–749 (1987).
Salkoff, L., et al., Trends in Neuroscience, 10:522–527 (1987).
Scanley, B. E., Biophys. J., 52:489–495 (1987).
Sheldon, R. S., et al., Mol. Pharmacol., 30:617–623 (1986).
Stuhmer, W., et al., European Biophysics Journal, 14:131–138 (1987).
Sumikawa, K., et al., Proc. Nat'l Acad. Sci. USA, 81:7994–7998 (1984).
Suzuki, H., et al., FEBS Letters, 228:195–200 (1988).
Ten Eick, R., et al., Biophys. J., 45:70–73 (1984).
Vassilev, P. M., et al., Science, 241:1658–1661 (1988).
Wigler, M., et al., Cell, 14:725–731 (1978).

FIG. 1A rh.sense

```
           10         20         30         40         50         60
    GAGACGGCCG GCGCCCGTGG GATGCGGGGA TCGGCCCCCG GGGCCCGCTGA GCCTTGAGCC
           70         80         90        100        110        120
    CGCTGCCCCA AGCCCTACGC CGAGCCGAGC CCGCACCGGC CTGCAGCCGC CCACCCCGGG
          130        140        150        160        170        180
    GCGCGGGCCG GGGACCATCA GCTTCCTTCC AGGCAACCTG AGGAGAGCCT GTGCCCCAG
          190        200        210        220        230        240
    AAGCAGGATG AGAAGATGGC AAACCTCCTG TTACCTCGGG GCACCAGCAG CTTCCGTAGG
          250        260        270        280        290        300
    TTCACCCGGG AGTCACTGGC GGCCATGGCC AAGCGAATGG CTGAAAAAGCA AGCCCGAGGA
          310        320        330        340        350        360
    GGTTCGGCCA CCTCACAGGA GAGCCGTGAG GGCCTGCAGG AGGAGGAGGC TCCCCGGCCC
          370        380        390        400        410        420
    CAGCTGGACC TACAGGCCTC CAAAAAGCTG CCAGATCTCT ATGGCAACCC ACCCCGAGAG
          430        440        450        460        470        480
    CTCATCGGGG AGCCCCTGGA AGACCTGGAC CCTTTCTATA GTACCCAGAA GACCTTCATC
          490        500        510        520        530        540
    GTGCTGAATA AGGGCAAAAC CATCTTCCGG TTCAGTGCCA CCAATGCCTT GTATGTCCTC
```

FIG. 1B

```
rh.sense
         550        560        570        580        590        600
AGCCCCTTCC ACCCCGTGCG CCGAGGCGGCC GTGAAGATCC TGGTACACTC GCTCTTTAGC
         610        620        630        640        650        660
ATGCTCATCA TGTGCACCAT CCTGACCAAC TGCGTGTTCA TGGCCCAGCA CGACCCTCCG
         670        680        690        700        710        720
CCTTGGACCA AATATGTTGA GTACACCTTC ACTGCCATCT ACACCTTTGA GTCTCTGGTC
         730        740        750        760        770        780
AAGATTCTAG CTCGAGGCTT CTGCCTGCAT GCATTCACCT TCCTTCGGGA CCCGTGGAAC
         790        800        810        820        830        840
TGGCTAGACT TCAGTGTGAT CATCATGGCA TACACAACTG AATTTGTGGA CCTGGGCAAT
         850        860        870        880        890        900
GTCTCAGCCT TACGCACCTT CCGAGTCCTC CGGGCCCTGA AAACTATATC GGTCATTTCA
         910        920        930        940        950        960
GGCCTGAAGA CCATCGTGGG AGCCCTAATC CAGTCTGTGA AGAAACTGGC CGATGTGATG
         970        980        990       1000       1010       1020
GTCCTCACTG TCTTCTGCCT CAGTGTCTTT GCCCTGCATT GGCCTGCAGCT CTTCATGGGC
        1030       1040       1050       1060       1070       1080
AACCTGAGGC ACAAGTGTGT GCGTAACTTC ACCGAGCTCA ATGGCACCAA TGGTTCCGTG
```

FIG. 1c r.h. sense

```
          1090       1100       1110       1120       1130       1140
     GAGGGCCGACG GCCTAGTCTG GAACTCCCTG GACGTCTACC TCAATGACCC AGCCAATTAC
          1150       1160       1170       1180       1190       1200
     CTGCTCAAGA ATGGCACCAC GGATGTGTTA CTATGTGGGA ACAGCTCTGA TGCCGGGACA
          1210       1220       1230       1240       1250       1260
     TGCCCTGAGG GCTATCGGTG CCTGAAGGCA GGTGAGAACC CAGACCACGG TTACACCAGC
          1270       1280       1290       1300       1310       1320
     TTCGACTCCT TCGCCCTGGG CTTCCCTTGCA CTCTTCCGCC TGATGACACA GGACTGCTGG
          1330       1340       1350       1360       1370       1380
     GAACGCCTAT ACCAGCAGAC CCTGAGGTCC GCAGGAAAGA TCTACATGAT CTTCTTCATG
          1390       1400       1410       1420       1430       1440
     CTCGTCATCT TTCTGGGCTC CTTCTACCTG GTGAACTTGA TCCTGGCTGT GGTGGCCATG
          1450       1460       1470       1480       1490       1500
     GCCTACGAGG AGCAAAACCA AGCCACCATC GCCGAGACGG AAGAGAAGGA GAAGCGCTTC
          1510       1520       1530       1540       1550       1560
     CAGGAGGCCA TGGAGATGCT CAAGAAGGAA CACGAGGCTC TCACCATCAG GGGTGTGGAT
          1570       1580       1590       1600       1610       1620
     ACCGTGTCCC GTAGCTCTCT GGAGATGTCT CCTTTGGCCC CAGTAACCAA CCATGAGAGA
``` rh.sense

```
      1630       1640       1650       1660       1670       1680
AAGAGCAAAA GGAGGAAACG ACTATCTTCG GGGACAGAGG ATGGTGGGGA TGACAGGCTC 1690       1700       1710       1720       1730       1740
CCCAAGTCGG ACTCAGAAGA TGGTCCCAGA GCATTGAATC AGCTCAGCCT CACCCATGGG 1750       1760       1770       1780       1790       1800
CTCAGCCGGA CATCCATGAG GCCCCGCTCG AGCCGAGGGA GCATTTTCAC GTTCCGAAGA 1810       1820       1830       1840       1850       1860
CGGGACCAAG GCTCTGAGGC GGACTTCGCA GATGACGAGA ACAGCACTGC GGGGGAGAGC 1870       1880       1890       1900       1910       1920
GAGAGCCACC GCACATCGCT GCTGGTACCC TGGCCCCTGC GCCATCCCAG CGCCCAAGGA 1930       1940       1950       1960       1970       1980
CAGCCCGGCC CTGGAGCCTC AGCTCCCGGT TACGTTCTCA ATGGCAAAAG GAACAGCACC 1990       2000       2010       2020       2030       2040
GTGGACTGCA ATGGGGTGGT TTCCTTGCTG GGGGCAGGTG ACGCAGAGGC CACCTCCCCA 2050       2060       2070       2080       2090       2100
GGGAGCTACC TTCTCCGCCC TATGGTGCTG GACCGACCCC CAGACACGAC CACTCCGTCA 2110       2120       2130       2140       2150       2160
GAGGAGCCCG GTGGGCCCCA GATGCTGACA CCTCAGGCTC CGTGTGCAGA TGGTTTTGAG
```

FIG. 1D

FIG. 1E rh.sense

```
          2170       2180       2190       2200       2210       2220
GAGCCCGGGAG CACGGCAACG GGCACTCAGC GCTGTCAGTG TCCTCACCAG CGCCCTGGAA
          2230       2240       2250       2260       2270       2280
GAGTTGGAGG AGTCCCATCG GAAGTGTCCA CCATGCTGGA ACCGCTTTGC CCAGCACTAC
          2290       2300       2310       2320       2330       2340
CTCATCTGGG AGTGCTGTCC ACTCTGGATG TCCATCAAGC AGAAGGTGAA GTTTGTGGTC
          2350       2360       2370       2380       2390       2400
ATGGACCCAT TTGCCGACCT CACTATCACC ATGTGCATCG TGCTCAATAC GCTCTTCATG
          2410       2420       2430       2440       2450       2460
GCTCTGGAGC ATTACAAACAT GACGGGCAGAG TTTGAGGAGA TGCTGCAGGT CGGAAAACCTG
          2470       2480       2490       2500       2510       2520
GTCTTCACGG GAATCTTCAC AGCGGAGATG ACCTTCAAGA TCATCGCCCT TGACCCCTAC
          2530       2540       2550       2560       2570       2580
TACTACTTCC AGCAGGGCTG GAATATCTTC GACAGCATCA TCGTCATCCT CAGTCTCATG
          2590       2600       2610       2620       2630       2640
GAGCTGGGGC TGTCCCGCAT GGGCAACTTG TCTGTGCTAC GTTCCTTCCG TCTGCTGCGG
          2650       2660       2670       2680       2690       2700
GTCTTCAAGC TGGCCAAGTC CTGGCCCACC CTGAACACGC TCATCAAGAT CATCGGAAAC
``` rh.sense

```
         2710       2720       2730       2740       2750       2760
   TCCGTGGGCG CCCTGGGGAA CCTGACCCTG GTGCTGGCCA TCATCGTCTT CATCTTCGCC
         2770       2780       2790       2800       2810       2820
   GTGGTGGGCA TGCAGCTCTT CGGCAAGAAC TACTCAGAAC TGAGGCACCG CATCAGCGAC
         2830       2840       2850       2860       2870       2880
   TCCGGCCTGC TGCCCCGCTG GCACATGATG GACTTTTTCC ACGCCTTTCCT CATCATCTTC
         2890       2900       2910       2920       2930       2940
   CGCATCCTCT GTGGGGAGTG GATCGAGACC ATGTGGGACT GCATGGAGGT GTCTGGGCAG
         2950       2960       2970       2980       2990       3000
   TCGCTGTGCT TGCTGGTCTT CCTGCTCGTC ATGGTCATTG GCAACCTTGT GGTCCTGAAT
         3010       3020       3030       3040       3050       3060
   CTCTTCTTGG CCTTGCTGCT CAGCTCCTTC AGCGCAGACA ACCTCACAGC CCCTGACGAG
         3070       3080       3090       3100       3110       3120
   GATGGGGAGA TGAACAACCT CCAGCTGGCC CTGGCTCGCA TCCAGAGGGG CCTGCGCTTT
         3130       3140       3150       3160       3170       3180
   GTCAAGCGGA CCACCTGGGA CTTCTGCTGC GGGATCCTGC GGCGGGCGACC TAAGAAGCCC
         3190       3200       3210       3220       3230       3240
   GCGGCTCTTG CCACCCACAG CCAGCTGGCC AGCTGTATCA CCGCCCCCAG GTCCCCACCA
```

FIG. 1F

FIG. 1G rh.sense

```
      3250       3260       3270       3280       3290       3300
CCCCCAGAGG TGGAGAAGGT GCCCCCAGCC CGCAAGGAAA CACGATTCGA GGAGGACAAG
      3310       3320       3330       3340       3350       3360
CGACCCGGCC AGGGCACCCC TGGGGATTCG GAGCCTGTGT GTGTGCCCAT CGCCGTGGCT
      3370       3380       3390       3400       3410       3420
GAGTCAGACA CTGAAGACCA GGAAGAGGAT GAAGAGAACA GCCTTGGCAC AGAGGAAGAG
      3430       3440       3450       3460       3470       3480
TCCAGCAAAC AGGAATCCCA AGTTGTGTCT GGTGGCCACG AGCCCTACCA GGAGCCCAGG
      3490       3500       3510       3520       3530       3540
GCCTGGAGCC AGGTGTCAGA GACCACGTCC TCTGAAGTCT GGGCCAGTAC ATCTCAGGCA
      3550       3560       3570       3580       3590       3600
GACTGGCAGC AAGAGCAGAA AACGGAGCCC CAGGCCCCGG GGTGCGGTGA GACCCCTGAG
      3610       3620       3630       3640       3650       3660
GACAGTTACT CCGAGGGCAG CACAGCTGAC ATGACCAACA CCGCCGACCT CCTGGAGCAA
      3670       3680       3690       3700       3710       3720
ATCCCAGACC TTGGTGAGGA CGTCAAGGAC CCAGAGGACT GCTTTACTGA AGGCTGCGTC
      3730       3740       3750       3760       3770       3780
CGACGCTGTC CCTGCTGCAT GGTAGACACA ACCCAGTCCC CAGGGAAGGT CTGGTGGCGA
``` rh.sense

```
        3790       3800       3810       3820       3830       3840
TTGCGCAAGA CCTGCTACCG CATCGTGGAG CACAGCTGGT TCGAGACTTT CATCATCTTC 3850       3860       3870       3880       3890       3900
ATGATCCTGC TCAGCAGTGG AGCCGCTGGCC TCGAGGACA TCTACCTGGA GGAGCGGAAG 3910       3920       3930       3940       3950       3960
ACCATCAAGG TTCTGCTGGA GTACGCGGAC AAGATGTTCA CCTACGTCTT TGTGTTGGAG 3970       3980       3990       4000       4010       4020
ATGCTGCTCA AGTGGGTGGC CTACGGCTTC AAGAAGTACT TCACCAACGC CTGGTGCTGG 4030       4040       4050       4060       4070       4080
CTGGACTTCC TGATTGTGGA CGTCTCGCTG GTCAGCCTCG TGGCAAAACAC CTTAGGCTTC 4090       4100       4110       4120       4130       4140
GCCGAAATGG GTCCCATCAA GTCACTGAGG ACACTGCGTG CACTTCGACC CCTGAGGGCC 4150       4160       4170       4180       4190       4200
TTGTCGAGAT TGAGGGCAT GCGGGTGGTG GTCAATGCGC TGGTGGGCGC CATCCCCTCC 4210       4220       4230       4240       4250       4260
ATCATGAACG TCCTCCTCGT CTGCCTCATC TTCTGGCTCA TCTTCAGCAT CATGGGGCGTG 4270       4280       4290       4300       4310       4320
AACCTCTTCG CCGGGAAGTT CGGTAGGTGC ATCAACCAGA CAGAAGGGGA CCTGCCTCTG
```

FIG. 1H

FIG. 1r rh.sense

```
         4330       4340       4350       4360       4370       4380
   AACTACACCA TCGTGAACAA CAAGAGTGAG TGCGAGTCCT TCAACGTGAC CGGAGAGTTG
         4390       4400       4410       4420       4430       4440
   TACTGGACCA AGGTGAAGGT CAACTTTGAC AACGTGGGAG CCGGGTACCT GGCCCTCCTG
         4450       4460       4470       4480       4490       4500
   CAGGTGGCGA CATTTAAAGG CTGGATGGAC ATCATGTATG CGGCTGTGGA CTCCAGAGGG
         4510       4520       4530       4540       4550       4560
   TATGAGGAGC AGCCGCAGTG GGAAGACAAC CTCTACATGT ACATCTACTT TGTCGTCTTC
         4570       4580       4590       4600       4610       4620
   ATCATCTTCG GCTCCTTCTT CACCCTCAAC CTCTTCATCG GTGTCATCAT TGACAACTTC
         4630       4640       4650       4660       4670       4680
   AACCAGCAGA AGAAAAAGTT AGGGGGCCAG GATATCTTCA TGACGGAGGA GCAGAAGAAG
         4690       4700       4710       4720       4730       4740
   TACTACAATG CCATGAAGAA GCTGGGCTCC AAGAAACCCC AGAAGCCCAT CCCACGGCCC
         4750       4760       4770       4780       4790       4800
   TTGAACAAGT ACCAGGGTTT CATATTCGAC ATTGTGACCA AGCAGGCCTT CGATGTCACC
         4810       4820       4830       4840       4850       4860
   ATCATGTTCC TCATCTGTTT GAACATGGTG ACCATGATGG TGGAGACAGA TGACCAGAGC
``` rh.sense

```
        4870       4880       4890       4900       4910       4920
  CCTGAGAAGG TCAACATCTT GGCCAAGATC AACCTGCTCT TCGTGGCCAT CTTCACAGGC
        4930       4940       4950       4960       4970       4980
  GAGTGTATTG TCAAGATGGC TGCCCTGCGC CACTATTACT TCACCAACAG CTGGAACATC
        4990       5000       5010       5020       5030       5040
  TTCGACTTTG TGGTGGTCAT CCTCTCCATT GTTGGCACTG TCCTCTCCGA CATCATCCAG
        5050       5060       5070       5080       5090       5100
  AAGTACTTCT TCTCCCCGAC ACTCTTCCGG GTCATCCGTC TGGCCAGGAT CGGCCGCATC
        5110       5120       5130       5140       5150       5160
  CTCAGGCTGA TCCGCGGAGC CAAGGGGATT CGCACGCTGC TCTTCGCCCT CATGATGTCC
        5170       5180       5190       5200       5210       5220
  CTGCCCGCCC TCTTCAACAT CGGCCTCCTC CTCTTCCTCG TCATGTTCAT CTACTCCATC
        5230       5240       5250       5260       5270       5280
  TTCGGCATGG CCAACTTCGC TTACGTCAAG TGGGAGGCCG GCATCGATGA CATGTTCAAC
        5290       5300       5310       5320       5330       5340
  TTCCAGACCT TCGCCAACAG CATGCTGTGC CTGTTCCAGA TCACCACATC AGCCGGCTGG
        5350       5360       5370       5380       5390       5400
  GACGGCCTCC TCAGCCCCAT CCTCAACACG GGGCCTCCCT ACTGCGACCC CAACCTGCCC
```

FIG. 1J

FIG. 1K rh.sense

```
        5410       5420       5430       5440       5450       5460
AACAGCAACG GCTCCCGGGG GAACTGTGGG AGCCCGGGCGG TGGGCATCCT CTTCTTCACC 5470       5480       5490       5500       5510       5520
ACCTACATCA TCATCTCCTT CCTCATCGTG GTCAACATGT ACATCGCCAT CATCCTCGAG 5530       5540       5550       5560       5570       5580
AACTTCAGCG TGGCCACCGA GGAGAGCACA GAGCCCCTGA GCGAGGACGA CTTCGACATG 5590       5600       5610       5620       5630       5640
TTCTATGAGA TCTGGGAGAA GTTCGACCCG GAGGCCACCC AGTTCATTGA GTATCTGGCC 5650       5660       5670       5680       5690       5700
CTGTCCGACT TTGCAGATGC CTTGTCTGAG CCGCTCCGCA TCGCCAAACC CAACCAGATA 5710       5720       5730       5740       5750       5760
AGCCTCATCA ACATGGATCT GCCCATGGTG AGCGGAGACC GTATCCACTG TATGGACATA 5770       5780       5790       5800       5810       5820
CTGTTCGCTT TCACCAAGAG GGTGCTCGGC GAGTCTGGGG AGATGGATGC CCTGAAGATC 5830       5840       5850       5860       5870       5880
CAGATGGAGG AGAAGTTCAT GGCGGCCAAC CCTTCCAAGA TCTCCTACGA GCCCATCACC 5890       5900       5910       5920       5930       5940
ACCACCCTGA GGAGAAAGCA CGAGGAGGTG TCGGCCACGG TCATCCAGCG TGCCTTCCGG
```

FIG. 1L

```
rh.sense
      5950       5960       5970       5980       5990       6000
AGGCACCTGC TGCAGCGCTC GGTGAAGCAT GCCTCCTTTC TCTTCCGCCA GCAAGCGGGC
      6010       6020       6030       6040       6050       6060
GGCAGTGGCC TCTCCGACGA GGATGCCCCT GAGCGGGAGG GCCTCATCGC CTACATGATG
      6070       6080       6090       6100       6110       6120
AATGGGAACT TCTCTCGGCG CAGTGCTCCG CTCTCCAGCT CCTCCATCTC CTCCACGTCC
      6130       6140       6150       6160       6170       6180
TTCCCCCCGT CCTACGACAG CGTCACGAGA GCCACCAGTG GACTTCCCTC GGTGCCGTGCG
      6190       6200       6210       6220       6230       6240
TCTGACTATA GCCGCAGCGA AGATCTTGCA CATCTCCAGA TAGGGACCGA
      6250       6260       6270       6280       6290       6300
GAGTCTATCG TGTGAACCTG GCCAGGGTGG CCGGGACGTT CGCCATTGTG CCCTGACGAA
      6310       6320       6330       6340       6350       6360
CCTTATGCAG TTAAAAACCAG TGTCGGCCGA GGCCTTCCTA GCTCTGCAGA TGAGCCTCCG
      6370       6380       6390       6400       6410       6420
GGTGGAGGAG CCTCGAGGCA GAGTTCCGTG TCTCTGTGTG GAAGCTGGAG GCAGCCGGAG
      6430       6440       6450       6460       6470       6480
GAGCCCTGGC TGGTGGAGGC CTGACCCTGG AGGCCCTGG CACCCTAGTA GCCGGGTCTG
```

FIG. 1M

```
r.h.sense
     6490       6500       6510       6520       6530       6540
GCCAGGGCAGC ACCGGCATGGC TCTCAAAAGC GACTCCGTCC CAGCTTCTGA GGTGGAATGG 6550       6560       6570       6580       6590       6600
GAAACACACT GTACATGTTG TGAACAAGCT TCCATAGATT TATTATATTT GATATTTTT 6610       6620       6630       6640       6650       6660
TACTTGAGCG AAGAACATCT TTTTCCATG AACATCAGCA GTTCACACTG CCTCTCCTTA 6670       6680       6690       6700       6710       6720
ACCCTGAGCA AGTGTCAACG GAGGTGCCAG AACTCGGCTC TCGAAGCTAA CGTGGGGATC 6730       6740       6750       6760       6770       6780
CATTGTACCC AAGGGGAGGG TCGTGCGTGG CTCCTGTTGC CTGGGCTGAG GAACCAGGAA 6790       6800       6810       6820       6830       6840
GGCCTAAGCA CTCCACTCAT ACACGCGTGT GTGTGCGAGC ACACTTCACA TGCTAGGGCG 6850       6860       6870       6880       6890       6900
GGACATAGGC CTGGGGGTCT TGGGGGAGCC GGGATCGCCT CAGGCAAATG TGGTCAGCGG 6910       6920       6930       6940       6950       6960
CTCTGAAGGA GGCAGGTTTT TCTTCCCAGC CCCCAAACGT GGGGTTCTTC CGGTGGAACT 6970       6980       6990       7000       7010       7020
CAGTCTGCGC TCCTGTTCTC CCCAGGACTC TGTTCTCCTG TTTTCTAGTC AGGCTTCACC
``` rh.sense

|  |  |  |  |  |  |
|---|---|---|---|---|---|
| 7030 | 7040 | 7050 | 7060 | 7070 | 7080 |
| TGAGGACAGT | GCTGCCAGAA | TTAAAAGCTC | TAGAGAGCTG | CCCCGGTCTC | AGAGATGAAT |
| 7090 | 7100 | 7110 | 7120 | 7130 | 7140 |
| TCTGCCCTTC | CTTCCTCTCC | TGGAAGAGTA | TTACTGTTGG | GGGTACGAGG | GAGGCAGCAC |
| 7150 | 7160 | 7170 | 7180 | 7190 | 7200 |
| CCCCTCACAG | CCAGGCACAT | AGGTCTCCCC | TAGTACACGG | CGGGCCCTGT | CCAAAGGCTG |
| 7210 | 7220 | 7230 | 7240 | 7250 | 7260 |
| AGGGAAGAGA | GGGCTGTTCC | ACATGGGCCG | CTGAACTGTG | TCCAGCTGTG | GGCAGCTGCA |
| 7270 | 7280 | 7290 | 7300 | 7310 | 7320 |
| CAGCAGAGGA | CGCCATCTCC | ATTTCCCAGG | CTCCCCCTGGG | GTCTCTGCCT | CTGACCGAGT |
| 7330 | 7340 | 7350 | 7360 | 7370 | 7380 |
| GTGAAGGGGA | TTCCCACTGG | GACTCCAACT | CCTCTTCAGA | CACTGTGGAA | GTGGGAGGGT |
| 7390 | 7400 | 7410 | 7420 | 7430 | 7440 |
| AGCCTGGCCC | TGCCTAGGAG | AGAGGCCCTG | GGTGGTCAGG | CATGGTTCTG | TGCCCTGGAA |
| 7450 | 7460 | 7470 | 7480 | 7490 | 7500 |
| GAGGACAAGC | CCTCCATCCC | ATCGGGAGGG | GAGGCAGTGT | GGGGTCTGGG | CCCAGCCCGG |
| 7510 | 7520 | 7530 | 7540 | 7550 |  |
| GGTCTGACTA | TCCCAGGGGT | CTTCTGAGAA | GGCTTTTTCA | GGAAAAAAAA | AAAAA |

FIG. 1N

```
BRII.AA                              LIMITS:  67  2000
RH.AA1                               LIMITS:  66  2000

```
BRII.AA                                           LIMITS:  67  2000
RH.AA1                                            LIMITS:  66  2000

```
BRII.AA                              LIMITS:  67  2000
RH.AA1                               LIMITS:  66  2000

```
BRII.AA                                      LIMITS:  67  2000
RH.AA1                                       LIMITS:  66  2000

```
BRII.AA                                    LIMITS:  67  2000
RH.AA1                                     LIMITS:  66  2000

```
BRII.AA                              LIMITS:  67  2000
RH.AA1                               LIMITS:  66  2000

```
BRII.AA                                    LIMITS:  67  2000
RH.AA1                                     LIMITS:  66  2000

```
BRII.AA                                      LIMITS:  67  2000
RH.AA1                                       LIMITS:  66  2000

```
BRII.AA                                                    LIMITS:  67  2000
RH.AA1                                                     LIMITS:  66  2000

```
BRII.AA                                  LIMITS:  67  2000
RH.AA1                                   LIMITS:  66  2000

```
BRII.AA                              LIMITS:  67  2000
RH.AA1                               LIMITS:  66  2000

NUCLEIC ACID ENCODING SODIUM CHANNEL PROTEIN

This application is a continuation of application Ser. No. 07/331,330, filed on Feb. 13, 1989, now abandoned.

BACKGROUND OF TEE INVENTION

The present invention relates generally to sodium channel proteins and more particularly to mammalian cardiac sodium channel proteins, to DNA sequences encoding sodium channel proteins, to the polypeptide products of recombinant expression of these DNA sequences, to peptides whose sequences are based on amino acid sequences deduced from these DNA sequences, to antibodies specific for such proteins and peptides, and to procedures for detection and quantitation of such proteins and nucleic acids related thereto, as well as procedures relating to the development of anti-arrhythmic and cardiotonic drugs based on interaction with such proteins.

Cardiac arrhythmias are responsible for 15-20% of the deaths in the United States; there are approximately 2,000,000 congestive heart failure patients in this country, with about 250,000 new cases each year. The cardiac sodium channel protein (also referred to as cardiac sodium channel) is intimately involved in most lethal arrhythmias and is the site of action of most clinically effective anti-arrhythmic drugs such as lidocaine, tocainide, quinidine, etc; and cardiotonic drugs that enhance cardiac contractility, including a new class of cardiotonic agents of which one (DP I 201-106) is presently in clinical trials.

Sodium channels are transmembrane proteins responsible for the early sodium permeability increase underlying the initial depolarization of the action potential in many excitable cells, such as muscle, nerve, and cardiac cells. Specifically, cardiac sodium channels are responsible for the excitation and conduction of the action potential (AP) in myocardial cells. Fozzard, H.A., et al., *Circ. Res.*, 56:475–485 (1985).

Cardiac sodium channel involvement in the generation of cardiac action potentials makes the channel a crucial site where anti-arrhythmic and cardiotonic agents act. The sodium channel is the most thoroughly characterized of the voltage-gated channels at this time. Six distinct neurotoxin or drug receptor sites have been characterized on the sodium channel, associated with channel pore or gating structures. Catterall, W.A., *Ann. Rev. Biochem.* 55:953–985 (1986); Catterall, W.A., *ISI Atlas of Science: Pharmacology* 190-195 (1988). Two functionally distinct populations of sodium channel subtypes have long been hypothesized to account for the physiological observation in certain mammalian cell preparations of two components of sodium current which have differing relative sensitivity to the neurotoxins, tetrodotoxin (TTX) and saxitoxin (STX). "TTX-sensitive" (TTX-S) sodium channels in mammalian nerve and in skeletal muscle are blocked by nanomolar concentrations of STX and TTX. "TTX-resistant" (TTX-R), or "TTX-insensitive" sodium channels, first observed in mammalian denervated skeletal muscle and in heart, have sodium currents and STX/TTX receptor sites which are blocked only by 2-3 orders of magnitude higher concentrations of TTX, i.e., in the 1-10 $\mu$M concentration range. TTX-resistant sodium channels have subsequently been found in widespread distribution in other immature mammalian nerve and in skeletal muscle cells lacking mature innervation. Electrophysiological and pharmacological studies have made it clear that TTX-resistant mammalian cardiac sodium channels have specialized properties distinct from TTX-sensitive sodium channels in nerve and skeletal muscle. The mechanisms by which drugs and neurotoxin agonists and antagonists act at the sodium channel and the development of general rules for how drugs interact with other ion channels having extensive homologies can be more readily studied once the actual structure of the sodium channel isoforms is more clearly understood. As used herein, the term "isoform" is used to mean distinct but closely related sodium channel proteins, which show strong homology in amino acid sequence and function and the term "subtype" is used to mean different major forms of sodium channels as identified by selective pharmacological agents showing different channel affinities.

Biochemical studies have shown [Catterall, W.A., *Ann. Rev. Biochem.*, 55:953–985 (1986)] that a large, approximately 260-kDa, glycoprotein $\alpha$-subunit is common to purified channel preparations from *Electrophorus electricus* (electric eel) electric organ, rat brain, rat skeletal muscle, and chick heart muscle. Rat brain contains, in addition, two smaller polypeptide subunits ($\beta$-1 and $\beta$-2) of molecular weight 36-kDa and 33-kDa respectively. The $\alpha$- and $\beta$-2 subunits are covalently attached by disulfide bonds. Rat skeletal muscle also contains at least one $\beta$-subunit. The $\alpha$-subunit alone appears to be responsible for specifying many of the key sodium channel functions. Noda, M., et al., *Nature*, 322:826–828 (1986); Agnew, W.S., *Nature*, 322:770–771 (1986); Goldin, A.L., et al., *Proc. Nat'l. Acad. Sci. USA*, 83:7503–7507 (1986). However, the $\beta$-subunits may modulate sodium channel functional properties as well. Krafte, D.S., et al., *J. Neurosci*, 8:(in press) (1988). Other studies [Catterall, W.A., et al., *Molec. Pharmacol.*, 20:533–542 (1981); Frelin, C., et al., *Pflugers Arch.*, 402:121–128 (1984); Rogart, R.B., *Ann. New York Acad. Sci.*, 479:402–430 (1986); Moczydlowski, E., et al., *Proc. Nat'l. Acad. Sci. USA*, 83:5321–5325 (1986)] have revealed the existence of multiple closely related isoforms of the sodium channel found in different animal species, in different tissues within the same species, and even in the same tissue.

Cloning studies of cDNAs encoding the sodium channel large $\alpha$-subunit from eel electroplax [Noda, M., et al., *Nature* 312:5990 (1984)], rat brain [Noda, M., et al., *Nature* 320:188–192 (1986)], and Drosophila [Salkoff, L., et al., *Trends in Neuroscience* (1987); Salkoff, L., et al., *Science* 237:744–749 (1987)] have demonstrated that: 1) the sequence of the $\alpha$-subunit consists of four repeated, highly homologous hydrophobic domains (each of which contains six transmembrane segments of S1–S6) separated by hydrophilic, nonrepeated intervening sequences; 2) considerable homology exists among the sequences from different species, with the greatest conservation existing among the four internally homologous domains; 3) the S4 segment of each homologous domain is positively charged, with four to eight lysine or arginine residues at every third position, which may be involved in channel gating [Greenblatt, R.E., et al., *FEBS* 193:125–134 (1985); Guy., R.H., et al., *Proc. Natl. Acad. sci. USA* 83:508–512 (1986); Noda, M., et al., *Nature* 312:5990 (1984)]; 4) in rat brain [Noda, M., et al., *Nature* 320:188–192 (1986); Kayano, T., et al., *FEBS Letters* 228:187–194 (1988)], three homologous brain mRNA sequences (designated as types I, II, and III)

encode distinct sodium channel isoforms in the same tissue; and 5) expression of mRNA injected into oocytes, coding for the α-subunit alone of the rat brain I, II, or III sodium channels, was sufficient to produce a functional voltage-activated sodium channel [Noda, M., et al., *Nature* 322:826–828 (1986); Suzuki, H., et al., *FEBS Letters* 228:195–200 (1988); Agnew, W.S., *Nature* 322:770–771 (1986); Goldin, A.L., et al., *Proc. Natl. Acad. Sci. USA* 83:7503–7507 (1986)] exhibiting many of the key properties of the native channel, including appropriate kinetics, voltage-sensitivity, ion selectivity, and sensitivity to the neurotoxin TTX. Different groups have found β-subunits important to varying extents to sodium channel function, making their role somewhat controversial. Catterall, W.A., *Ann. Rev. Biochem.* 55:953–985 (1986); Agnew, W.S., *Nature* 322:770–771 (1986); Goldin, A.L., et al., *Proc. Natl. Acad. Sci. USA* 83:7503–7507 (1986); Messner, D.J., et al., *J. Biol. Chem.* 261:14882 (1986); Auld, V.J., et al., *Neuron* (in press) (1988); and Stuhmer, W., et al., *Eur. Biophys. J.* 14:131–138 (1987).

The detection of three separate cDNA clones has led to the identification of three structurally distinct sodium channel isoforms in rat brain. Noda, M., et al., *Nature* 320:188–192 (1986). Two further distinct isoforms have been detected in rat skeletal muscle [Barchi, R.L., *Probing the Molecular Architecture of the Voltage-Dependent Sodium Channel* in "*The Molecular Biology of Receptors, Pumps, and Channels: Pharmacological Targets*," ASPET Meeting Abstracts; Abstract No., Aug. 1988]. The molecular relationship of these isoforms found in rat brain and in rat skeletal muscle to the sodium channel isoforms found in rat heart remains unknown.

Attempts have been made to clarify the functional relationship of the three rat brain isoforms. When rat brain mRNA species were injected into *Xenopus oocytes*, it was found that II and III both induced similar sodium currents [Noda, M., et al., *Nature*, 322:826–828 (1986); Suzuki, H., et al., *FEBS Letters*, 228:195–200 (1988)]; and that these currents were also grossly similar to those produced upon injection of rat brain poly(A+) mRNA. Stuhmer, W., et al., *Eur. Biophys. J.*, 14:131–138 (1987). However, injection of rat brain I sodium channel mRNA into oocytes induced only small currents. Further, recent studies have detected characteristics of the sodium current which differ when induced by sodium channel-specific mRNAs than when induced by those from total rat brain poly (A+) mRNA. Mandel, G., et al., *Proc. Nat'l. Acad. Sci.*, 85:924–928 (1988); Auld, V.J., et al., *Neuron*, 1:449–461 (1988); Krafte, D.S., et al., *J. Neurosci.*, 8:(in press) (1988). These conflicting results make it difficult to determine the functional relationship between the three rat brain sodium channel mRNA species and the functional properties of the sodium channel isoforms they encode. Furthermore, biophysical descriptions of nerve membrane sodium permeability do not provide a clearcut role for as many as three sodium channel isoforms. For instance, voltage-clamp studies of the sodium current in mammalian nerve cells have most frequently been interpreted in terms of only a single population of sodium channels. Aldrich, R., et al., *J. Neurosci.*, 7:418–431 (1987).

It remains unclear 1) which structural domains of the human TTX-resistant cardiac sodium channel account for their specialized functional properties; 2) what the role of multiple cardiac sodium channel isoforms in cardiac action potential excitation and conduction is; and 3) the nature of the interaction of pharmacological agents with the small sequence domains which form the receptors. Further, it remains unclear as to how these TTX-sensitive and TTX-resistant sodium channel isoforms may arise.

Two apparently different brain and cardiac sodium channel isoforms may represent post-translational modifications of a single polypeptide molecule; the same α-subunit may be present in both cardiac and nerve sodium channel isoforms, and differences may arise from the presence of other small β-subunits making up the channel protein; and/or distinct α-subunits may account for the differences between the TTX-sensitive and TTX-resistant isoforms of the sodium channel. These distinct α-subunits may be encoded by distinct gene sequences which arise from a family of closely related genes which are differentially expressed in various tissues, or from alternative splicing of a single gene.

There thus continues to exist a need in the art for information concerning the ways in which these TTX-sensitive and TTX-resistant sodium channel isoforms arise, as well as specific information concerning the primary structural conformation of cardiac sodium channel protein and concerning other sodium channel proteins such as might be provided by knowledge of human, rat, and other mammalian DNA sequences encoding the same.

Availability of such DNA sequences would make possible the application of recombinant methods to the large scale production of the proteins in procaryotic and/or eukaryotic host cells, as well as DNA-DNA, DNA-RNA, and RNA-RNA, hybridization procedures for the detection, quantification and/or isolation of nucleic acids associated with these proteins. Possession of cardiac sodium channel and related sodium channel proteins and/or knowledge of the amino acid sequences of the same would make possible, in turn, the development of monoclonal and polyclonal antibodies thereto (including antibodies to protein fragments or synthetic peptides modeled thereon) for the use in immunological methods for the detection and quantification of the proteins in fluid and tissue samples, as well as for tissue specific delivery of substances such as labels and therapeutic agents to cells expressing the proteins; as well as allowing for the development of new anti-arrhythmic and cardiotonic drugs.

BRIEF SUMMARY OF THE INVENTION

The present invention provides novel purified and isolated nucleic acid sequences encoding rat cardiac sodium channel protein. In presently preferred forms, novel DNA sequences comprise cDNA sequences encoding rat cardiac sodium channel protein. Specifically, three cDNA sequences, together, encode for the full length rat cardiac sodium channel. These sequences are contained in plasmids designated pRH3-1, pRH4-23, pRH14-31, and deposited Feb. 9, 1989, with the American Type Culture Collection, 12301 Parklawn Drive, Rockville, Md. 20852 in accordance with the U.S. Patent and Trademark Office's requirements for microorganism deposits under Accession Nos. 67885; 67886; and 67887, respectively. Alternate DNA forms such as genomic DNA, and DNA prepared by partial or total chemical synthesis from nucleotides as well as DNA with deletions or mutations, is also within the contemplation of the invention. Also provided are novel messenger RNA (mRNA) sequences, specifically rat heart sodium channel mRNA species.

Association of DNA sequences provided by the invention with homologous or heterologous species expression control DNA sequences, such as promoters, operators, regulators and the like, allows for in vivo and in vitro transcription to form mRNA which, in turn, is susceptible to translation to provide sodium channel proteins, and related poly- and oligo-peptides in large quantities. In a presently preferred DNA expression system of the invention, sodium channel encoding DNA is operatively associated with a regulatory promoter DNA sequence allowing for in vitro transcription and translation in a cell free system to provide, e.g., a 260 kD sodium channel protein and smaller forms of these proteins, including 30–40 kD species. In a presently preferred mRNA expression system, mRNA species are injected directly into Xenopus oocytes thereby allowing for in vitro translation to form a functional sodium channel capable of demonstrating functional characteristics of native sodium channels including ion selectivity, gating-kinetics, voltage-sensitivity, and sensitivity to pharmacological agents such TTX.

Incorporation of DNA sequences into *procaryotic* and *eucaryotic* host cells by standard transformation and transfection processes, potentially involving suitable viral and circular DNA plasmid vectors, is also within the contemplation of the invention and is expected to provide useful proteins in quantities heretofore unavailable from natural sources. Use of mammalian host cells is expected to provide for such post-translational modifications (e.g., truncation, glycosylation, and tyrosine, serine or threonine phosphorylation) as may be needed to confer optimal biological activity on recombinant expression products of the invention.

Novel protein products of the invention include polypeptides having the primary structural conformation (i.e., amino acid sequence) of sodium channel proteins, as set forth in FIG. 2, as well as peptide fragments thereof and synthetic peptides assembled to be duplicative of amino acid sequences thereof. Proteins, protein fragments, and synthetic peptides of the invention are projected to have numerous uses including therapeutic, diagnostic and prognostic uses and will provide the basis for preparation of monoclonal and polyclonal antibodies specifically immunoreactive with sodium channel proteins. Preferred protein fragments and synthetic peptides include those duplicating regions of cardiac sodium channel proteins which are unique to cardiac sodium channel functions. The proteins of the invention are also expected to find utility in developing more effective anti-arrhythmic and cardiotonic drugs.

Also provided by the present invention are polyclonal and monoclonal antibodies characterized by their ability to bind with high immunospecificity to cardiac sodium channel proteins and to their fragments and peptides, recognizing unique epitopes which are not common to other proteins especially other ion channel proteins. The antibodies of the invention can be used for affinity purification of cardiac sodium channel from cells including human, canine or rat cardiac cells.

Also provided by the present invention are novel procedures for the detection and/or quantification of isoforms or normal, abnormal, or mutated forms, of sodium channel, as well as nucleic acids (e.g., DNA and mRNA) associated therewith. Illustratively, antibodies of the invention may be employed in known immunological procedures for quantitative detection of sodium channel proteins in fluid and tissue samples, of DNA sequences of the invention (particularly those having sequences encoding sodium channel proteins) that may be suitably labelled and employed for quantitative detection of mRNA encoding these proteins.

Among the multiple aspects of the present invention, therefore, is the provision of (a) novel rat cardiac sodium channel protein DNA sequences set out in FIG. 1, as well as (b) DNA sequences which hybridize thereto under hybridization conditions of the stringency equal to or greater than the conditions described herein and employed in the initial isolation of cDNAs of the invention, and (c) DNA sequences encoding the same allelic variant, or analog sodium channel protein polypeptides through use of, at least in part, degenerate codons. Correspondingly provided are vital or circular plasmid DNA vectors incorporating such DNA sequences and procaryotic and eucaryotic host cells transformed or transfected with such DNA sequences and vectors as well as novel methods for the recombinant production of sodium channel proteins through cultured growth of such hosts and isolation of these proteins from the hosts or their culture media.

Other aspects and advantages of the present invention will be apparent upon consideration of the following detailed description thereof which includes numerous illustrative examples of the practice of the invention, reference being made to the drawing wherein:

BRIEF DESCRIPTION OF THE DRAWINGS

FIG. 1 provides a 7555 base pair nucleotide cDNA sequence for a rat cardiac sodium channel, derived from three overlapping cDNA clones, designated as pRH31, pRH4-23, and pRH14-31;

FIG. 2 provides the deduced sequence of 2019 amino acid residues for cardiac sodium channel protein and provides a comparison to the deduced amino acid sequence for rat brain II cDNA.

DETAILED DESCRIPTION

The following examples illustrate practice of the invention.

Example 1 relates to hybridization of mRNA from rat brain and rat cardiac muscle with a 2500-nucleotide long anti-sense cRNA probe coding for the carboxy-terminal region of the rat brain II sodium channel α-subunit.

Example 2 relates to [$^3$H]-STX binding measurements of brain and cardiac muscle preparations of STX receptors.

Example 3 relates to hybridization of mRNA from rat brain and rat cardiac muscle with the rat brain II sodium channel cRNA probe under increasingly stringent hybridization conditions; example 4 relates to hybridization studies using slot blot analysis; and example 5 relates to hybridization studies using melting curves measurements.

Example 6 relates to hybridization studies demonstrating the existence of multiple isoforms in rat cardiac muscle.

Example 7 relates to the construction and screening of a cDNA library from newborn rat heart; example 8 relates to the isolation and characterization of positive cDNA clones which span the length of the rat cardiac sodium channel; and example 9 relates to heterologous expression of positive cDNA encoding for a rat "TTX-R cardiac" sodium channel isoform.

Example 10 relates to use of cardiac-specific rat cardiac sodium channel cDNAs as probes to isolate human cardiac sodium channel isoforms; and, example 11 relates to electrophysiological and pharmacological characterization of the expression product of cloned human cardiac sodium channel isoforms.

Example 12 relates to the generation of antibodies against cardiac sodium channel isoforms; and, example 13 relates to use of antibodies against cardiac sodium channel isoforms.

Example 14 relates to the development of antiarrhythmic and cardiotonic agents.

The examples which follow are for illustrative purposes only and are not intended in any way to limit the scope of the invention.

Prerequisite to cloning the rat cardiac sodium channel (using cross-hybridization of rat brain sodium channel II cRNA probes to screen a newborn rat cardiac cDNA library for cardiac sodium channel clones) was developing a procedure for obtaining a strong cross-hybridization signal for the rat brain cRNA probes with the rat cardiac sodium channel sequence. The pioneering molecular biology studies of rat brain sodium channel obtained only weak cross-hybridization signals on Northern blots of mRNA from other tissues. Noda, M., et al., *Nature*, 320:188–192 (1986) obtained only faint hybridization with rat heart mRNA, and no hybridization with rat skeletal muscle, with a 90-hour exposure of autoradiograms from their Northern blots; Goldin, A.L., et al., *Proc. Nat'l. Acad. Sci. USA*, 83:7503–7507 (1986) also obtained only faint hybridization signals with rat heart and skeletal muscle mRNA, using a 60-hour exposure. Examples 1–5 relate to hybridization studies for optimizing conditions for obtaining strong signals on Northern blots with only a 1-hour autoradiogram exposure. An efficient cRNA probe was used for quantification of mRNA properties and for cDNA cloning of rat cardiac sodium channel. A new means was developed to quantify specific and background hybridization strength on Northern and dot blots under differing stringency conditions. It was found that an unusually narrow range of temperature of only 2°–3° C. optimized the hybridization signal to noise ratio. At higher stringency (i.e., increased temperature), the background decreased, but the specific cross-hybridization signal also decreased steeply. At lower stringency (i.e., decreased temperature) the specific signals increased, but this was obscured by a steeply increasing background.

EXAMPLE 1

Hybridization of mRNA from Rat Brain and Rat Cardiac Muscle with a 2500-nucleotide Long Anti-Sense cRNA Probe Coding for the Carboxy-Terminal Region of the Rat Brain II Sodium Channel α-Sub-unit Rat brain and heart mRNA was isolated from the brains and hearts of 6-day old rats by the guanidine isothiocyanate procedure of Chirgwin, J.M., et al., *Biochemistry*, 18:5294–5299 (1979). Rat brains and hearts were rapidly dissected, and immediately frozen in liquid nitrogen. They were then immersed in guanidine isothiocyanate and immediately homogenized with a Polytron homogenizer at half speed for 15–30 seconds.

The RNAs were fractionated by electrophoresis through a 1.2% agarose gel in the presence of formaldehyde. This size-fractionated RNA was transferred from the gel to nitrocellulose [Thomas, P.S., *Biochem.*, 77:5201–5205 (1980)] and the resulting filter was probed with a 2500-nucleotide long anti-sense [$^{32}$P]-labeled cRNA probe [pEAF8, bases 3580 to 6080 of Noda, et al., *Nature*, 320:188–192 (1986), from Goldin, A.L., et al., *Proc. Nat'l. Acad. Sci. USA*, 83:7503–7507 (1986)] complementary to the carboxy-terminal coding region of the rat brain II sodium channel α-subunit mRNA.

The [$^{32}$P]-labeled cRNA probe was synthesized using T7 RNA polymerase, from 1 μg of SalI-linearized sodium channel cDNA inserted into a pGEM1 vector, in the presence of 70 μCi of [$^{32}$P]-UTP (400 Ci/mmol), 500 μM of ATP, CTP, GTP and 12 μM UTP. The cRNA probe had a specific activity of about $15 \times 10^6$ cpm/μg.

Hybridization was carried out at 55° C., in the presence of 50% formaldehyde, 5 X SSC (1 X SSC=0.5M NaCl, 0.05M sodium citrate, pH=7.0), 50 mM NaPO$_4$ pH=6.5, 0.1% SDS, 5 X Denhardt's, 50 μg/ml sheared denatured salmon sperm DNA, 250 μg/ml wheat germ tRNA (type V, Sigma) and $2.5 \times 10^6$ cpm/ml of labeled cRNA probe. Washes were at temperatures ranging from 50°–70° C. in the presence of 30% formamide, 0.1 X SSC, 50 mM NaPO$_4$ pH 6.5 and 0.1% SDS. Lengths of hybridization bands (in kb) were determined in comparison to the position of RNA molecular weight standards (Bethesda Research Laboratories, Gaithersberg, Md.) and the position of the 18S and 28S ribosomal RNA. Autoradiography for heart and liver was conducted for 16 hours, and for brain for 1 hour.

Northern blots show bands corresponding to hybridization of the cRNA probe with an mRNA species of about 9 kB for both rat brain and heart. Consistent with previous findings [Noda, M., et al., supra; Goldin, A.L., et al., supra, the hybridization band signal for rat cardiac mRNA was of considerably lower strength than for rat brain mRNA—a 32-fold longer exposure of rat heart mRNA was required to obtain the bands of approximately equivalent intensity. In the previous studies, it remained unresolved whether the differing hybridization signals reflected differences in: 1) the abundancy of sodium channel mRNA species in rat brain and heart, or 2) the extent of homology of the rat brain II sodium channel cRNA probe with the mRNAs encoding rat brain TTX-sensitive and rat heart TTX-resistant sodium channel subtypes. In Examples 2–5 below, it is demonstrated that option 2 is the correct one.

EXAMPLE 2

[$^3$H]-STX Binding Measurements of Brain and Cardiac Muscle Preparations

In most of the tissue preparations where the TTX-resistant sodium channel subtype is found, it is present along with the TTX-sensitive sodium channel subtype. These preparations include mammalian newborn and denervated mammalian skeletal muscle, skeletal muscle cells in tissue culture, and adult cardiac muscle cells. Distinguishing between the possible origins of the two sodium channel subtypes which may lead to differing hybridization signals is therefore complicated by their simultaneous presence in these tissue preparations. Similarity of the hybridization signals for mRNA from rat brain and a non-brain preparation containing both the TTX-sensitive and TTX-resistant sodium channel subtypes might, for instance, reflect their common TTX-sensitive sodium channels while simultaneously obscuring differences arising from the TTX-resistant sodium channel subtype. However, while studying the ontogeny [see Example 6] of sodium channel subtypes in rat cardiac muscle, it was found that only the TTX-resistant sodium channel subtype was expressed in young newborn rats.

[³H]-saxitoxin (STX) receptor measurements demonstrate that in newborn 6-day old rats there is a single population of "high-affinity" [³H]-STX receptor in brain and "low affinity" [³H]-STX receptor in cardiac muscle. STX and TTX are otherwise frequently used interchangeably because of their ability to block sodium channels in a similar fashion. Ritchie, J.M., et al., *J. Physiol.*, 269:341–354 (1977). Labeled STX, rather than TTX, was used due to the ability to tritium-label STX to a very high specific activity that is 200–500 times more radioactive than commercially available labeled TTX. Total [³H]-STX binding was determined from identical homogenate samples (2–3 mg wet weight of tissue) exposed to labeled [³H]-STX ranging in concentration from 0 to 3 nM (brain) or 0 to 40 nM (heart). Non-specific [³H]-STX binding was measured in the presence of an excess of unlabeled STX (2 μM) and was the non-displaceable linear portion of total binding. Membrane homogenate samples were prepared with a Polytron homogenizer, centrifuged at 30,000×g for 20 minutes, and resuspended with a glass-glass homogenizer in an assay solution containing 154 mM choline chloride and 10 mM MOPS. [³H]-STX binding measurements were determined using a combined centrifugation/filtration assay providing high-resolution of low-affinity [³H]-STX receptor sites as described in Rogart, R.B., et al., *Proc. Nat'l Acad. Sci.*, 80:1106–1110 (1983).

Both sets of data points were jointly fitted by non-linear regression to the sum of two components: 1) a hyperbolic saturable component ($B_{max}/[K_d+\{T\}]$), where $\{T\}$ is toxin concentration, $B_{max}$, is maximum specific binding, and $K_d$ is the equilibrium dissociation constant, 2) a linear component ($b \cdot \{T\}$) corresponding to non-specific [³H]-STX binding. Presence of single populations of [³H]-STX receptors for these binding curves was tested for by Scatchard plots; and by fitting the data to alternative models consisting of one and two populations of [³H]-STX receptors, and determining by F-test the number of populations of [³H]-STX receptors [Rogart, R.B., et al., *Brain Res.*, 329:314–318 (1985)] which best described the data.

[³H]-STX binding measurements of brain and cardiac muscle preparations from 6-day old rats revealed single populations of "high-affinity" [³H]-STX receptors in brain and "low-affinity" [³H]-STX receptors in cardiac muscle. The presence of single populations of [³H]-STX receptors is confirmed by the straight line Scatchard plots obtained. For rat brain membrane, the maximum specific [³H]-STX binding capacity ($B_{max}$) value is 498 fmole/mg protein, and the equilibrium dissociation constant ($K_d$) is 0.25 nM. For rat heart membrane, the $B_{max}$ value is 131 fmole/mg protein and the $K_d$ value is 11.4 nM. Thus, [³H]-STX receptors on rat cardiac and brain sodium channels have a 46-fold difference in affinity for [³H]-STX. These high- and low-affinity [³H]-STX receptors have a corresponding 500–1000 fold difference in affinity for unlabeled TTX, determined in competition studies. Thus, cardiac muscle from 6-day old rats provides a preparation with an apparently homogeneous population of TTX-resistant sodium channels.

The sodium channel protein abundancies for rat brain and heart of 498 and 131 fmole/mg protein, respectively, differ by a factor of about 4-fold. This protein abundancy difference of only about 4-fold is insufficient to explain the 32-fold difference in hybridization signal intensity obtained in Example 1. This intensity difference need not actually reflect the protein abundancy for a number of reasons. Two factors may contribute to the difference observed in hybridization signal intensity. First, the same mRNA species may be encoding identical α-subunits for the two isoforms of the sodium channel in rat brain and heart, but the sodium channel mRNA level may be considerably lower in rat heart than in rat brain. Second, brain and heart sodium channel mRNA species may encode distinct α-subunits. Weak hybridization then results because the cardiac mRNA species is only partially homologous to the brain cRNA probe. Example 3 demonstrates that the observed difference is due to the fact that different sodium channel mRNAs are present in 6-day old rat brain and heart and that these channels are products of distinct gene sequences.

EXAMPLE 3

Hybridization of mRNA from Rat Brain and Rat Cardiac Muscle with Rat Brain II Sodium Channel α-Subunit cRNA Under Increasingly Stringent Hybridization Conditions To determine whether the difference in hybridization bands reflected divergent sodium channel sequences, the intensity of hybridization for rat cardiac and brain mRNA was compared under increasingly stringent conditions. Hybridization signals decreasing in parallel reflect similar or identical mRNA species, while signals decreasing at different rates reflect structurally distinct mRNA species. Identical samples of rat brain and heart mRNA were hybridized with the rat brain cRNA probe of Example 1 under the same conditions, but then washed at 50° C. and 65° C., respectively. While the hybridization band signal at about 9-kb for rat brain mRNA decreases only by about 33% under these conditions, the signal for rat heart mRNA is almost entirely abolished. This indicates that weak hybridization results because the cardiac mRNA species is only partially homologous to the probe.

Example 4 presents a more detailed quantitative analysis of the nature of the different hybridization signals obtained in Example 3.

EXAMPLE 4

Hybridization Studies Using Slot Blot Analysis

For this quantitative study of hybridization signal strengths, slot blot analysis of mRNA applied directly to nitrocellulose paper was used. This probe is estimated to be five to ten fold more sensitive than Northern blot analysis. Berent, S.L., et al., *BioTech.*, 3:208–220 (1985).

For a rare mRNA species (such as for the sodium channel mRNA), non-specific background hybridization may contribute a significant fraction of the slot blot hybridization signal. This corresponds to a summation of the background distributed diffusely along the lanes in Northern blots. In the latter, the specific hybridization signal can be distinguished since it stands out above background as a discrete band. It is therefore important to determine a quantitative measure of the fraction of the slot blot signal which results from non-specific background hybridization.

For the slot blot hybridization measurements described below, a novel approach was employed to allow detection of rare mRNAs. Background hybridization was measured for the labeled cRNA probe by a parallel measurement in the presence of a 20–40 fold excess of unlabeled cRNA probe. Specific hybridization was determined as the difference between the total hybridization signal and the background hybridization signal.

Total RNA (in 4.1M formaldehyde and 16.66 X SSC) from 6-day old rat whole brain, cardiac muscle, and liver was applied directly to nitrocellulose in 6.0 mm² slots using S&S Slot Blot II apparatus in five 1:3 serial dilutions of starting amounts (5 μg brain; 15 μg heart; 45 μg liver). Hybridization and wash conditions were as for the Northern blots described above. A total signal consisting of specific hybridization of the cRNA probe with mRNA and non-specific background hybridization was measured. For brain and heart mRNA, a significant specific hybridization signal is present since slot blot signal intensity is significantly higher. For liver mRNA, used as a control, there is no significant specific hybridization.

EXAMPLE 5

Hybridization Studies Using Melting Curve Measurements

The effects of increasingly stringent conditions upon hybridization were measured using the labeled cRNA probe hybridized to larger samples of mRNA dot blotted onto nitrocellulose circles. Melting curves were determined using mRNA (30 μg brain; 75 μg heart; and 30 μg liver) blotted onto 25 mm nitrocellulose circles, as described for slots, and hybridized with the [$^{32}$P]-labeled cRNA probe. Filters in wash solution (as described above for Northern blots) were washed 2-3 times at 45° C., and then subjected to increasing temperatures from 40° C. to 97° C. in 3° C. increments. After 10 minutes the wash solution was completely removed and the total amount of [$^{32}$P]-labeled cRNA probe melted and released from hybrids on filter paper was determined by scintillation counting. [$^{32}$P]-labeled cRNA probe melted from non-specific background hybrids was determined by hybridizing in the presence of a 20-40 fold excess of unlabeled cRNA. Specific melted [$^{32}$P]-labeled cRNA probe was determined as the difference between total and background amounts, obtained in triplicate samples. The cumulative amount of specific [$^{32}$P]-labeled cRNA probe melted as a function of temperature was determined from the summation of labeled cRNA probe released at lower temperatures.

The increased surface area of the 25 mm circles used in these studies allowed for detailed quantitation of the amount of probe melted at different temperatures. The hybrids were subjected to increasing temperatures from 45° C. to 97° C. The specific signal was determined as described above, by parallel measurements in the presence of a 20-40 fold excess of unlabeled cRNA probe. The total and non-specific background radioactivity released was determined as a function of temperature for rat brain and heart mRNA attached to nitrocellulose circles, respectively. Non-specific hybrids are released from both preparations in a single monophasic peak melting at about 50° C. The radioactivity resulting from specific melted hybrids, was determined as the difference between the total and the non-specific hybridization.

Two further control studies were conducted. For liver mRNA, no significant difference was found for total and non-specific background melting curves. This indicates that no significant specific hybridization occurs with the rat brain II sodium channel probe to liver mRNA. The background signal remains the same with labeled cRNA probe alone, or upon addition of excess unlabeled cRNA probe. For hybridization of anti-sense cRNA probe to sense strand cRNA, the melting curve showed a single component with $T_m$ value of 79° C., corresponding to the rat brain mRNA high $T_m$ component showing homologous hybridization.

The specific hybrids between the rat brain II sodium channel cRNA probe and rat brain mRNA were found to melt in a biphasic distribution with respect to temperature, peaking at 57° C. and 79° C., respectively. This suggests at least two rat brain mRNA species encoding isoforms of the TTX-sensitive brain sodium channel.

For RNA:RNA hybrids, the $T_m$ decreases by about 1.4° C. per 1% decrease in homology [Bodkin, D.K., et al., *Virology*, 143:55-62 (1985)], indicating an 84% base sequence homology between the two major fractions of rat brain mRNA species. This corresponds well with previous findings from cloning studies and complete sequence analysis.

The melting curve for rat heart mRNA shows a single component with $T_m$ value of 52° C., suggesting the existence of a distinct mRNA sequence with lower homology (about 81% to rat brain II) than the two brain mRNA sequences, and which encodes a structurally different TTX-resistant cardiac sodium channel. Thus, at least two major sodium channel mRNA species are present in approximately equal amounts in rat brain mRNA. This heterogeneity in sodium channel mRNA species contrasts with the apparent biochemical homogeneity of the purified sodium channel protein preparations from rat brain. Hartshorne, R.P., et al., *Proc. Nat'l Acad. Sci. USA*, 78:4620-4624 (1981).

The results described above show remarkable agreement with the nucleotide homology determined from direct cloning studies which determined an 84% nucleotide sequence homology between the rat brain II sodium channel mRNA species and the mRNA species encoding each of the rat brain I and III sodium channels. The peak melting at 57° C., therefore probably corresponds to hybrids of the rat brain II cRNA probe with mRNA species encoding both rat brain I and III sodium channels. Since the relative abundance of the rat brain III sodium channel is less than that of the rat brain I channel, a larger component of the 57° C. melting peak is associated with hybrids of cRNA probe:mRNA of rat brain I sodium channel.

EXAMPLE 6

Studies Demonstrating the Existence of Multiple Sodium Channel Isoforms in Rat Heart As a Function of Physiological Development Hybrid melting curves were obtained by hybridizing a [$^{32}$P]-labeled rat brain II cRNA probe, of Example 1, with newborn and adult rat heart mRNA, and then subjecting these hybrids to increasingly stringent conditions resulting from increased temperature. [$^{32}$p]-label from dissociated hybrids was then measured as a function of temperature, determining the temperature at which hybrids melt. As indicated in Example 5, studies with newborn rat heart mRNA demonstrate a single major peak, corresponding to the presence of only one major sodium channel mRNA species. In contrast, hybrid melting curves with adult rat heart mRNA demonstrate 3-4 peaks, demonstrating the existence of multiple sodium channel isoforms appearing during development of rat heart. This is consistent with the appearance of a second population of high-affinity [$^3$H]-STX receptors at days 9-10 in rat heart.

For adult rat heart, where both TTX-sensitive and TTX-resistant sodium channel subtypes are present, at least three species of expressed sodium channel mRNA were found, i.e., a melting curve with three distinct components with $T_m$ values of 52° C., 57° C., and 62° C. was obtained. The component at 52° C. for adult cardiac mRNA matches one at 52° C. for newborn rat cardiac mRNA. The component at 57° C. matches the one at 57° C. in newborn rat brain mRNA, indicating perhaps that the same or a very similar mRNA species is expressed in brain and heart, or that this mRNA species arises as neuronal contamination of the adult rat cardiac mRNA preparation.

In addition, hybridization of adult rat skeletal muscle mRNA was characterized. Previous studies had found only weak or absent hybridization on Northern blots for rat skeletal muscle. A large component, melting at 54° C., and a smaller one, melting at 67° C., were found, indicating that despite the presence of TTX-sensitive sodium channel subtypes in both rat skeletal muscle and brain, their major corresponding mRNA species are only about 83% homologous, comparable to that found for cardiac and brain mRNA species encoding TTX-resistant and TTX-sensitive sodium channel subtypes.

EXAMPLE 7

Construction and Screening of cDNA Library from Newborn Rat Heart

A. Construction

A cDNA library was constructed in the lambda-Zap vector (Stratagene, LaJolla, Calif.), starting with mRNA obtained from newborn rat hearts obtained at post-natal day 6. Total RNA was generated by the guanidine isothiocyanate procedure of Chirgwin, J.M., et al., *Biochem.*, 18:5294 (1979). Poly (A+) mRNA was obtained by oligo(dT) chromatography. First strand cDNA synthesis was accomplished with avian myeloblastosis reverse transcriptase (A-MRT). Poly(dT) and random hexamer-oligonucleotides were used to prime two separate 15 μg mRNA samples. Second strand cDNA synthesis was primed by a "5' hairpin loop", which was subsequently cleaved with $S_1$ nuclease after elongation of the strand with DNA polymerase. Equal amounts of double-stranded cDNA originated from the oligo(dT) and random hexamer primed mRNA. The cDNA greater than 3 kb were then combined and ligated into the lambda-Zap vector.

B. Screening

Screening of cDNA libraries was accomplished by hybridizing the rat cardiac sodium channel cRNA probes with nitrocellulose replicas of plaques using the procedure of Benton, W.D., et al., *Science*, 196:180 (1977) at 45° C., 1×SSC and 0.1% SDS. Plaques positive on duplicate filters were purified by limiting dilution through two additional screenings.

EXAMPLE 8

Isolation and Characterization of Positive cDNA Clones Which Span the Length of the Newborn Rat Cardiac Sodium Channel One million plaques of the newborn rat heart cDNA library were initially screened with the rat brain II cDNA probe. Four positive cDNA clones were detected. In Northern analysis, 3 clones hybridized more strongly to rat brain mRNA than rat heart mRNA (and were subsequently identified by sequencing as rat brain I cDNA clones). One (pRH4-23) hybridized more strongly to rat heart mRNA than rat brain mRNA. The original nitrocellulose replica filters were subsequently rescreened with pRH4-23, and an additional 27 cardiac specific positive cDNA clones were isolated. Two of these (pRH14-31 and pRH12-31) in combination with each other spanned the entire sodium channel sequence, except for about the first 230 bases of the 5' end.

A second cDNA library was generated using the Gubler-Hoffman method. This library was primed with random hexamers and with three 20-base long oligonucleotides taken from the determined cardiac sodium channel sequence and located at approximate nucleotide positions 600, 900, and 4000. Primary screening of this cDNA library with pRH12-31 yielded 15 positive cDNA clones. Secondary screening was accomplished with a 600-base long probe taken from the 5' end of pRH12-31 and detected 7 positive cDNA clones. One of these clones (pRH3-1) was found to originate at base 900 and extend 2-kb in the upstream direction into the 5' non-coding region.

The clones cover the full-length sequence as follows:

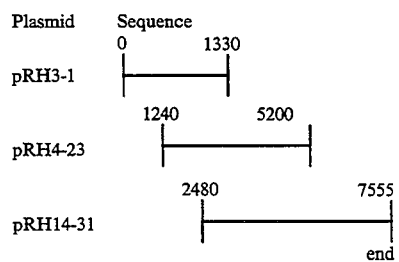

The top strand sequence of bases 0 through 7555 is set out in the accompanying FIG. 1. The initial ATG of the coding region appears in the box at bases 196–198. A termination codon (TGA) is indicated by the box at bases 6253–6255. FIG. 2 provides a comparison of the 2019 residue deduced amino acid sequences for the rat cardiac channel protein (lower line) encoded by the cDNA with that encoded by cDNA for rat brain II (upper line). Connecting lines indicate homology, while dots indicate non-identical but "conserved" residues.

EXAMPLE 9

Heterlogous Expression of Positive cDNA Encoding for a Rat "TTX-R cardiac" Sodium Channel Isoform A. Construction of Full Length Clone for Expression A full length DNA sequence for use in recombinant expression of the sodium channel protein may be partially or wholly manufactured from nucleotide bases using the sequence information provided in FIGS. 1 and 2. See, e.g., Alton, PCT Patent Application Publication No. WO83/04053; Nov. 24, 1983.

It is presently contemplated that certain of the 27 positive clones obtained in Example 8 having advantageous restriction endonuclease sites will be useful to construct a full length clones as follows. cDNA clone pRH11-71 (nt 639-3165) can be digested with Bcl I (795) and Sma I (in the cloning plasmid polylinker region), and the resulting fragment (795-3165) can be inserted into the 5' terminal clone, pRH3-1, (nt 0-1330) cut with Bcl I (795) and Eco RV (polylinker). The resulting product (0-3165) can be digested with Bam HI (3150) and/a Bam HI fragment derived from clone pRH4-23, (nt 3150-5200) can be inserted, resulting in a product extending from 0-5200. This product can be digested with BstEII (single site, 4825), and a BstEII fragment derived from the 3' terminal clone, pRH14-31, (4825 to end) can be added, utilizing polylinker sites on the 3' end, to complete the full-length construction.

B. Expression of Full-length Clone

Messenger RNA from full-length cDNAs can be synthesized using an SP6 vector system. Following capping and phosphorylation, this mRNA can be micro-injected into *Xenopus oocytes*. Goldin, A.L., et al., *Proc. Nat'l. Acad. Sci. USA,* 83:7503–7507 (1986); Sumikawa, K., et al., *Proc. Nat'l. Acad. Sci. USA,* 81:7994–7998 (1984). Three days after injection with 60–120 ng of mRNA in 60 nl of solution, oocytes can then be tested for sodium currents with a two microelectrode voltage-clamp. $I_{Na}$ can then be further characterized to see whether it exhibits the specialized properties of cardiac $I_{Na}$, such as relative resistance to TTX.

Further, it is possible to inject homogenous clonally-derived mRNA encoding TTX-R human cardiac sodium channels, where expression of even a small fraction may result in significant functional TTX-R cardiac sodium channels. Other mature specialized functional properties of the cardiac sodium channels may still be expressed, even if TTX-resistance is not, which can be determined by detailed electrophysiological and pharmacological characterizations. Because sodium channel β-subunits may be required for modulation of specialized functions or to develop secondary and tertiary structure (i.e., folding) required to be released from the endoplasmic reticulum and Golgi apparatus, whole mRNA or smaller molecular weight subfractions of whole mRNA can be added back to determine whether the combined expression products now altered channel function.

The foregoing examples and the background cited in Example 11 demonstrate that there are multiple isoforms of sodium channels in rat heart, surpassing the diversity previously recognized as pharmacological subtypes. It is anticipated that the cDNAs for each isoform can be cloned and expressed in heterologous systems so that for each its pharmacological properties can be determined. Major previous pharmacological advances have resulted from this approach for other membrane receptors, such as in the development of drugs specific to subtypes of nicotinic/muscarinic, acetyl choline, adrenergic, or histaminergic receptors. For cardiac sodium channel isoforms, this approach allows for the design of potentially isoform-selective agents with uniquely tailored specificity: 1) acting at cardiac sodium channels, without deleterious side effects at nerve sodium channels; and 2) targeting particular subpopulations of cardiac sodium channel isoforms selectively in diseased myocardium over normal myocardium.

Discovery of the sequence of cardiac sodium channel cDNA, permits the development of more site-specific drugs including:

1) cardiac-specific Class I anti-arrhythmic agents with even lower neuromuscular side effects and a greater therapeutic ratio;
2) isoform-specific agents, which may underly arrhythmogenic foci, or may be expressed in ischemic tissue (i.e. "fetal" isoforms), by leaving normal isoforms unaltered; side effects (e.g. negative inotropy) may be avoided entirely;
3) sufficient quantities of sodium channel isoforms may be synthesized to allow classical structure-function analysis, eventually permitting chemical synthesis of drugs specific for individual isoforms at selected sites;
4) isoform-specific cDNA and antibody probes for localizing isoforms involved in arrhythmogenesis in pathological studies, imaging studies, or open chest epicardial mapping;
5) isoform-specific antibodies as acute anti-arrhythmic agents, i.e. for otherwise intractable arrhythmias in the critical 24–48 hours post myocardial infarction; and
6) cardiotonic agents (e.g. DPI 201–106) may be developed along principles similar to the above examples.

The following example relates to the characterization of the molecular properties of cardiac-specific sodium channel isoforms, to a correlation of their unique structural characteristics with their specialized functional properties, and to providing the fundamental basis for the rational development of anti-arrhythmic and cardiotonic agents acting at cardiac sodium channels.

EXAMPLE 10

Use of Cardiac-Specific Rat Cardiac Sodium Channel cDNAs as Probes to Isolate Human Cardiac Sodium Channel Isoforms A. Construction of Human Cardiac cDNA Libraries Human cardiac sodium channel isoforms can be cloned by using a human cardiac cDNA library. By cloning a full-length cDNA and expressing in heterologous systems, the structure-function relationships of the sodium channel can be characterized. The large 9-kb size of the sodium channel mRNA necessitates use of methods which optimize synthesis of large cDNA clones. To obtain cDNA clones spanning the entire sequence of the sodium channel consists of three steps: 1) construction and screening of a lambda-Zap bacteriophage cDNA library using several approaches tailored to selection of low abundance, long length cDNAs encoding TTX-R cardiac sodium channels, 2) rescreening of the lambda-Zap library with probes from positive clones; and 3) construction of a library by primer extension to obtain any missing segments.

A bacteriophage cDNA library is constructed using the lambda-Zap vector (Stratagene), accommodating up to 10-kb inserts, and modifications of the Gubler-Hoffman method. *Gene,* 25:263–269 (1983). The screening of this phage library is simpler than a plasmid vector cDNA library, since plaques may be plated at higher density and hybridized with lower background. The lambda-Zap phage vector contains the cDNA insert within an internal partial M13 plasmid sequence, which can be "rescued" from positive phage plaques by co-infection with an M13 helper phage, allowing direct subcloning into Bluescript plasmids. This circumvents the usual disadvantage of a phage cDNA library, namely, the need to subclone into plasmids to generate enough cDNA for further sequencing or probe generation.

In the usual Gubler-Hoffman method of cDNA library generation, single-stranded cDNA is transcribed with avian myeloblastosis reverse transcriptase (A-MRT), using oligo-(dT) as primer. This is modified by using cloned Maloney-Murine Reverse Transcriptase (M-MRT) which optimizes cDNA length over A-MRT and by priming first strand cDNA snythesis with random hexanucleotides ("hexamers"), allowing cDNA 1st strand synthesis to begin at interior portions of the mRNA. This circumvents three problems: i) the frequency of cDNAs for the rare abundance sodium channel is increased, since multiple initiation sites are possible along its long length; ii) cDNA clones need not extend from a poly(A) initiation site and over the non-protein coding region before they can be detected; iii) upstream clones are obtained. Double-stranded (ds) cDNAs primed with random hexamers are mixed with an equal quantity of dscDNAs primed with oligo (dT), to generate a combined cDNA library. The cDNA can be size selected (3–10 kb) by non-denaturing gel electrophoresis in low-melting agarose prior to vector ligation. (ds)-cDNA synthesis in the Gubler-Hoffman method has been further simplified to a single reaction mixture containing DNA polymerase I, DNA ligase, and RNase H. This method also uses RNase H nicked RNA as primer for DNA polymerase, avoiding the problematic step of $S_1$ nuclease cleavage of the 5' "hairpin loop" which results in loss of 5' sequence B. Screening Human Cardiac cDNA Library with TTX-R Rat Cardiac cDNA or cRNA Probes Screening of cDNA libraries can be accomplished by hybridizing rat cardiac sodium channel cRNA probes described above with nitrocellulose replicas of plaques using the procedure of Benton, et al., Science, 196:180 (1977). Plaques positive on duplicate filters can be purified by limit dilution through two additional screenings. Two further stages of screening are then employed: 1) Southern blots of positive cDNA inserts can confirm that selected inserts indeed hybridize to labeled rat cardiac sodium channel cRNA probes; 2) Northern blots can further verify the identity of these putative human cardiac sodium channel positive cDNA clones. cRNA probes generated from positive cDNA inserts can be hybridized with mRNA from human and rat heart, brain, and skeletal muscle. Hybridization to a 9-kb transcript corresponding to the sodium channel should be observed, and the intensity of hybridization at high stringency should be greater for cardiac mRNA than for brain or skeletal muscle mRNA, demonstrating cardiac-specificity of the positive cDNA clones.

C. Construction of Full Length cDNA Clone for Expression

Full-length cDNA clones can be constructed by selective cleavage of overlapping clones by appropriate restriction enzymes, and ligation of fragments directly or with synthesized oligonucleotide linkers. Full-length cDNAs can be inserted into SP6 vectors (e.g., pGEM2, Bluescript) or any vector capable of accepting an insert as large as the 6-kb of the sodium channel protein coding region.

D. Expression of TTX-R Human Cardiac Sodium Channel in Xenopus Oocytes

1. Expression of the TTX-R Human Cardiac Sodium Channel in Xenopus Oocytes:

The expression of cardiac sodium channel can be accomplished as described infra in Example 9, section B.

2. Mammalian Cell Transfection and Expression of the TTX-R Human Cardiac Sodium Channel:

Full length cDNA clones for TTX-R human cardiac sodium channel can be inserted into appropriate expression vectors and used in gene transfer experiments to set up transient and stable expression systems in mammalian cell lines.

a) Transient Expression Systems:

A transient expression system [Gorman, C., DNA Cloning: A Practical Approach, Oxford, IRL Press, 143–190 (1985)], can be used due to the rapidity possible with this assay. Messenger RNA and protein synthesis can be analyzed within 48 hours after the introduction of DNA. Large quantities of specific mRNA (as much as 1% of total cellular mRNA) frequently can be expressed. In contrast, construction of stable transformed cell lines is lengthy, and the levels of expression of mRNA are frequently below that obtained with transient systems. Several questions are most efficiently addressed in these systems: 1) which cell types and vectors are most efficient in expressing transfected cardiac sodium channel cDNAs; 2) which cell types are capable of expressing mature TTX-R cardiac sodium channels which retain their native functional properties; and 3) which of the chimeric sodium channel cDNAs (described below) generated from TTX-S and TTX-R sodium channel isoforms are able to specify synthesis of functional sodium channels.

Sodium channel cDNA can be introduced into SV40 expression vectors (e.g., pSV2) into COS-7 cells, using the calcium phosphate [Wigler, M., et al., Cell, 14:725 (1978)] or DEAE-Dextran [Lopata, M.A., et al., Nucl. Acids Res., 12:5707 (1984)] transfection procedures. Previous studies with transfection of n-Acetyl choline receptor (nAChR) genes found significant transcription of AChR mRNA to levels of about 1% of total mRNA in transfected cells. Claudio, T., et al., Science, 238:1688–1694 (1987); Claudio, T., et al., Cloning and transfer of acetylcholine receptor genes in: Molecular Neurobiology: A Short Course, McKay, R. D., Ed., Bethesda, Neuroscience Society, 22–27 (1984). Transfected cells can be tested for their level of expression of cardiac sodium channel mRNA species, and for the expression of TTX-R sodium flux and low-affinity [$^3$H]-STX receptors. Other common cell types can also be tested for transient transfection, e.g., CHO cells, mouse fibroblasts (L cells, 3T3 or 3T6 cells), HeLa cells, neuroblastoma, L6 muscle cells, etc. Studies with primate cells utilize SV40 expression vectors, whereas studies with other cells utilize Rous Sarcoma Virus vectors (i.e., pRSV), which is the most ubiquitous promotor for efficient transient expression. A number of means for increasing transfection efficiency are available, if required, to increase the fraction of cells and/or their individual yield in expressing sodium channels [Selden, R., Current Protocols in Mol. Biol., (ed F.M. Ausubel):9-41–943 (1987); Muckett, M., et al., J. Virol., 49:857–863 (1984)].

b) Stable Expression Systems:

Stable cell lines [Claudio, T., et al., Science, 238:1688–1694 (1987); Claudio, T., et al., Cloning and transfer of acetylcholine receptor genes in: Molecular Neurobiology: A Short Course, McKay, R. D., Ed., Bethesda, Neuroscience Society, 22–27 (1984)] with transfected sodium channel cDNAs can be established for detailed electrophysiological, pharmacological, and biochemical characterization. This is particularly useful for characterization of cloned TTX-R cardiac and chimeric sodium channel cDNAs by patch-clamp methods, since in transient systems, only a small percentage of cells express transfected sodium channels. Transient expression experiments can be used to determine which viral expression vectors are most efficient in particular cell types. For instance [Gorman, C., DNA Cloning: A Practical Approach, Oxford, IRL Press, 143–190 (1985)], cells can be co-transfected with sodium channel cDNA in a pSV or pRSV vector, along with a dominant selectable marker such as gpt or neoR (i.e., in vectors prSV-gpt or pRSV-neo). The cells will be subcultured into a selective medium two days following transfection, and then once every 4–5 days thereafter until discrete colonies can be seen on transfected plates, requiring 1–2 months to establish stable cell lines. Cells selected by dominant marker can then be tested for expression of sodium channels as well.

3. Functional Assays for Sodium Channel Expression:

Transfected cells can be tested for expression of low-affinity [$^3$H]-STX receptors, TTX-R sodium fluxes, and other pharmacological characteristics of the TTX-R cardiac sodium channel, which have been previously measured with high sensitivity. Previous studies [Bonner, T.I., et al., *Science*, 237:527–532 (1987)] with other membrane proteins suggest that their level of expression is well within the range where sodium channels can be detected with present assays. Bonner, T.I., et al., *Science,* 237:527-532 (1987). Some modifications may be required, e.g., transfected COS-7 cells lose their surface adhesion which will require development of a column sodium flux assay, rather than the monolayer assay normally employed. When stable transfection is successful, electrophysiological characterization of these clonally-derived cardiac sodium channels can be undertaken by patch-clamp techniques.

EXAMPLE 11

Electrophysiological and Pharmacological Characterization of Cloned Human Cardiac Sodium Channel Isoforms With the Identification and Selective Expression of Multiple Cardiac Sodium Channels The mammalian cardiac action potential progresses during physiological development from: 1) a slow upstroke velocity, dependent upon Ca, and entirely insensitive to TTX in embryonic heart; to 2) a rapid upstroke velocity, dependent upon sodium, and sensitive to TTX in the 1-10 uM range. Only low-affinity [$^3$H]-STX receptors are present at birth in rat heart; and a second population of high-affinity [$^3$H]-STX receptors appears at days 9-10. Levels of both receptors are developmentally regulated. Furthermore, dV/dt of the cardiac action potential (slope of phase 0 depolarization) is specialized in different regions of the heart to meet the requirements of cardiac action potential propagation. Noble, D., *The initiation of the Heartbeat,* Oxford Univ. Press (1975). The role played by differential expression of cardiac sodium channel isoforms in determining these excitability properties can be elucidated by selectively probing for each specific isoform.

Considerable evidence already suggests involvement of multiple sodium channel isoforms in cardiac action potential excitation, as in rat brain [Noda, M., et al., *Nature* 320:188-192 (1986)]: 1) electrophysiological studies have demonstrated two single channel conductances [Scanley, B.E., et al., *Biophys. J.* 52:489-495 (1987); Ten Eick, R., et al., *Biophys J.* 45:70-73 (1984)]; two sets of kinetic constants [Verkhratsky, A.N., et al., *Fiziol Zh* 33:44-49 (1987)]; and $I_{Na}$ components with different sensitivities to TTX [Ten Eick, R., et al., *Biophys J.* 45:70-73 (1984); Pidoplichko, V.I., *Ten. Physiol. Biophys* 5:593-599 (1986)] and to STX [Hanck, D.A., *Biophys J.* 53:534a (1988)]; 2) developing canine heart becomes more sensitive to anti-arrhythmic agents and less sensitive to TTX, suggesting a change in sodium channel isoforms expressed [Morikawa, YU., et al., *Cir. Res.* 57:354-361 (1985)]; and 3) neonatal cardiocytes in tissue culture express sodium channels which show only a fast inactivation component, whereas adult ventricular and Purkinje fiber sodium channels show two-component (fast and slow) inactivation. Kohhardt, M., et al., *J. Membrane Biol* 103:283-291 (1988).

It is controversial whether TTX-S sodium channel isoform(s) (with high-affinity [$^3$H]-STX receptors) are involved in cardiac excitation. Rogart, R.B., et al., *Ann NY Acad Sci* 479:402-430 (1987). Numerous electrophysiological studies have failed to detect a corresponding TTX-S $I_{Na}$ component [Fozzard, H.A., et al., *Circ. Res.* 56:475-485 (1985); Cohen, D.J., et al., *J. Gen. Physiol.* 78:383-411 (1981)]. One proposal has suggested that high-affinity [$^3$H]-STX receptors result from nerve contamination of cardiac membrane preparations. Catterall, W.A., et al., *Molec. Pharm.* 20:526-532 (1981). However, high-affinity [$^3$H]-TTX receptors also arise in cultured embryonic rat cardiac cells, in the absence of nerve tissue. Renaud, J.F., et al., *J. Biol. Chem.* 258:8799-8805 (1983). Another possibility is that these high-affinity [$^3$H]-STX receptors are associated with precursor forms of the sodium channel. Rogart, ROB., et al., *Ann NY Acad Sci* 479:402-430 (1987).

By analyzing comparative properties of different isoforms of the sodium channel, it can be determined precisely which amino acid differences underly the unique functions and drug specificities of TTX-R cardiac versus TTX-S nerve sodium channels, thereby providing a fundamental basis for developing cardiac-selective anti-arrhythmic and cardiotonic agents. Further, it is possible to generate and express a series of chimeric cDNAs [Imoto, K., et al., *Nature* 324:670-672 (1986); Price, E.M., et el., *Identification of the Amino Acids Involved in Ouabain Resistance by Site-Directed Mutagenesis. in "The Molecular Biology of Receptors, Pumps, and Channels: Pharacological Targets", ASPET Meeting Abstracts* (1988)] of TTX-S and TTX-R sodium channel isoforms, replacing a series of regions of the TTX-R sodium channel sequence with homologous TTX-S sodium channel sequences. By then determining which of the channel chimeras changes from a TTX-R to TTX-S sodium channel, for instance, it will be possible to localize the structural domain involved in TTX-senstivity. Similarly, the structural domains controlling anti-arrhythmic/local anesthetic agent sensitivity can be determined.

Having localized these sites in the chimeric cDNAs, site-directed mutagenesis can be used to identify the specific amino acid sequences in the sodium channel making up these drug receptors. This approach circumvents difficulties in using site-directed mutagenesis alone: 1) assessing whether function is altered directly or indirectly due to allosteric influences at a remote site; 2) the exceedingly large size of the sodium channel (about 200 amino acids) make site-directed mutagenesis impractial without some idea of which site to alter.

A. Comparative Properties of Human Cardiac Sodium Channel Isoforms

These studies can provide a quantitative comparison of the detailed electrophysiological properties and pharmacological sensitivities of the TTX-R human cardiac sodium channel isoforms. The various isoforms which have been cloned can be compared in detail by expressing their cDNAs in oocytes and transfected mammalian cells. Previous studies using the two-microelectrode voltage clamp of oocytes have shown that fast sodium current are inadequately controlled to permit a quantitative comparison. Krafte, D.S. et al., *J. Neurosci,* 8:(in press); Auld, V.J., et al., *Neuron,* (in press) (1988). Hence, a single microelectrode switching voltage-clamp can be used to control oocyte internal potential, and a macroscopic patch electrode can then be used to measure INa. Stuhmer, W., et al., *Eur. Biophys. J.,*

14:131–138 (1987). A simple kinetic model which describes well the characteristics of macroscopic $I_{Na}$ and single channel recordings can be used to provide a framework for comparing the electrophysiological characteristics of isoforms and their physical significance. This model can describe a state diagram for the opened and closed conformations that the sodium channel may occupy, and the voltage-dependent transitions which may occur between states. The ability of a kinetic model to accurately describe several isoforms can help discriminate between multiple alternative models available. Pharmacological agents (anti-arrhythmic and cardiotonic agents, toxins, etc.) acting at the sodium channel can then be compared for various isoforms. Interaction of agents can be studied with: 1) $I_{Na}$ and single channel recordings; 2) sodium fluxes; and 3) radiolabeled drug binding (i.e., [$^3$H]-batrachotoxin binding [Sheldon, R.S., et al., Mol. Pharmacol, 30:617–623 (1986)] and competition with other agents. Again, a comprehensive quantitative model can be used to compare various isoforms, and provide a physical interpretation for the differing drug sensitivities of various isoforms.

B. Chimeric cDNAs and Site-Directed Mutagenesis of TTX-R/TTX-S Sodium Channel Isoforms The specific amino acids in the sodium channel sequence responsible for their functional characteristics and interaction with agents altering sodium channel function can be localized. A single chimeric or "hybrid" gene from two genes encoding closely related but different sodium channel isoforms can be constructed. Chimeras can be constructed by combining portions from human TTX-R cardiac and TTX-S skeletal muscle or brain sodium channel cDNAs into a new single chimeric cDNA. The polymerase chain reaction (PCR) [Erlich, H.A., et al., Nature, 331:461–462 (1988)] can be used to generate portions of the TTX-S sodium channel cDNAs from published sequences, to be combined with human TTX-R portions forming the hybrid cDNAs. The chimeric cDNAs generated can then be expressed in heterologous systems, and their properties examined.

By analyzing the changes in properties of the resultant "hybrid" polypeptide, the various functional domains of the sodium channel can be mapped. For instance, in a series of chimeras, portions of the TTX-R cardiac sodium channel sequence can be systematically replaced by homologous TTX-S sequence. The resulting chimeric cDNA can be expressed and can be determined when the TTX-sensitivity changes from TTX-R to TTX-S, thereby elucidating the structural domains conferring TTX-sensitivity. Similarly, chimeras for the polypeptide and alkaloid neurotoxins, anti-arrhythmic agents, pore structures controlling conductances, gate structures determining activation and inactivation, etc. can be constructed and characterized. Once the structural domains conferring these properties have been localized in chimeras, site-directed mutagenesis can be used to pinpoint specific amino acids involved. Previously this approach has been used: 1) to localize ion transport to a region of the gamma subunit of nAChRs [Imoto, K., et al., *Nature,* 324:670–672 (1986)]; and 2) to map the structural domains and amino acids controlling ouabain-sensitive and insensitive Na-K ATPases. Price, E.M., et al., Identification of the Amino Acids Involved in Ouabain Resistance by Site-Directed Mutagenesis in "The Molecular Biology of Receptors, Pumps, and Channels: Pharmacological Targets", ASPET Meeting Abstracts, Aug., 1988; Kent, R., et al., *Science,* 237:901–903 (1987). Provided herein are the amino acid sequences and structures of the rat cardiac sodium channel, which can directly provide the basis for future design of site-specific drugs targeted to particular human cardiac sodium channal isoforms.

EXAMPLE 12

Generation of Antibodies Against Sodium Channel Isoforms

Antibodies against sodium channels from brain, skeletal muscle, and eel electric organ have been used for further protein purification [Casadei, J.M., et al., *J. Biol. Chem.,* 261:4318–4323 (1986)], for morphological localization, and for identification of structure-function relationships. Vassilev, P.M., et al., *Science,* 241:1658–1661 (1988). It has not previously been possible to isolate sufficient quantities of cardiac sodium channel protein to allow for complete purification and to provide sufficient antigen for antibody production. Cloning of cardiac sodium channel provides two approaches to allow eventual purification of sodium channel and to generate antibodies against cardiac sodium channel sequence (in particular rat and human cardiac sodium channel): 1) cDNAs encoding about 40 kDa portions of the cardiac sodium channel sequence can be incorporated into expression vectors which are used to infect *E. coli.* Large quantities of this *E. coli* can be grown, expressing a fusion protein of the sodium channel sequence and another polypeptide encoded by the vector. This fusion protein can then be purified and used as antigen [Perbol, B., *A Practical Guide to Molecular Cloning,* New York, John Wiley, 750–779 (1988)]; polypeptides consisting of 10–30 amino acids determined from the cardiac sodium channel sequence may be synthesized by chemical means, and used as antigen. Erlich, H.A., et al., *Nature,* 331:461–462 (1988).

EXAMPLE 13

Use of Antibodies Against Cardiac Sodium Channel Isoforms

A. Purification of Cardiac Sodium Channel Isoforms

Purification of large quantities of the sodium channel protein [Casadei, J.M., et al., *J. Biol. Chem.,* 261:4318–4323 (1986)] can be achieved by immunoprecipitation or by immuno-affinity chromatography. This will provide sufficient protein of adequate purity so that isolation to homogeneity can then be achieved by conventional means used in purification of sodium channels from other sources. This approach has been used in purifying un-degraded rabbit skeletal muscle sodium channels. Casadei, J.M., et al., *J. Biol. Chem.,* 261:4318–4323 (1986). Purified sodium channels can then be used to study subunit composition, post-translational modification (which may build upon sequence differences to create distinct isoforms), and classical structure-function relationships. For the latter, heterologous expression in mammalian cells, followed by purification with antibodies can be useful to produce intact and functional cardiac sodium channel isoforms in sufficient milligram quantities for structure analysis. Lester, H.A., *Science,* 241:1057–1063 (1988).

B. Biosynthesis of Cardiac Sodium Channels

Isolation of intermediates will allow the steps in assembly and post-translational modification to be elucidated. Merlie, J.P., et al., *J. Membrane Biol.,* 91:1–10 (1986). Rat heart cells and culture can be pulse-labeled with [$^{35}$S]-methionine. At various selected times for the next three days, cells can be harvested, nascent sodium channel proteins can be isolated by precipitation with sodium channel-specific antibodies. The nascent proteins can then be characterized biochemically.

C. Functional Studies on the Effect of Antibody Binding to Sodium Channels

Antibodies generated against particular peptide segments can be studied to determine their effect on sodium channel function. Vassilev, P.M., et al., *Science*, 241:1658–1661 (1988). Such antibodies may show interactions resembling other drugs and toxins, altering particular channel functions in a use- and voltage-dependent fashion.

D. Development of Antibodies as Acute Anti-Arrhythmic Agents

Such antibodies can be developed for use as highly specific acute anti-arrhythmic agents. Antibodies generated against small sequences of the soduim channel have already been shown to perturb channel function. Antibodies can be generated against synthetic polypeptides believed to be putative structures where anti-arrhythmic agents act. Such antibodies can be tested in electrophysiological studies for their anti-arrhythmic action and cardiac specificity.

E. Morphological Localization of Cardiac Sodium Channel Isoforms

Localization of cardiac sodium channel isoforms can be achieved by immunofluorescence and immuno-electron microscopy. In situ hybridization or in situ transcription can be performed using cDNA/cRNA probes generated from cardiac sodium channel cDNAs. This will allow determination of synthesis, and tissue and subcellular densities and localization of the mRNAs encoding various cardiac sodium channel isoforms.

The density and distribution of sodium channel isoforms (and their associated mRNAs) involved in normal cardiac impluse conduction can be determined, i.e., in ventricle, atria, septum; conducting system and Purkinje cells; SA and AV nodes, etc. Furthermore, changes in predominance of isoforms of the sodium channel associated with patho-physiological conditions can be determined, such as ischemia, hypertrophy, injury, fibrillation, intractable arrhythmias, etc. These studies can demonstrate which "fetal" or other cardiac sodium channel isoforms arise with these disorders. Drugs can then be developed specifically targeted to individual isoforms.

EXAMPLE 14

Development of Anti-Arrhythmic and Cardiotonic Agents

Studies can be initiated for design and testing of new drugs selected for their specific interaction with individual cardiac sodium channel isoforms. A systematic approach to drug design depends upon knowing the three-dimensional structure of their intended receptor sites. At present, most such drug designs depend upon synthesis of congeneric series, systematically making minor variations in substituents at particular groups. Computer-aided design of drugs targeted to receptor structures has been developed. Marshall, G.R., et al., *Trends in Pharm. Sci.*, 9:285–289 (1988).

Various approaches to the design of anti-arrhythmic and cardiotonic agents with specificity for particular isoforms of cardiac sodium channels are possible. cDNA cloning may be used to identify unique cardiac sodium channel isoforms in this multigene family. Each isoform may be expressed in heterologous cell systems to determine its unique electrophysiological properties and pharmacological sensitivities [Lester, H.A., *Science*, 241:1057–1063 (1988)] further correlating variations in primary structural domains with their associated specialized functions. Anti-arrhythmic and cardiotonic agents with enhanced therapeutic ratio may then be selected and designed based upon their interaction with individual sodium channel isoforms associated with known cardiac regions and functions and having distinct primary sequences. Examples of this approach include: 1) arrhythmias in human fetal hearts appear to have a different anti-arrhythmic sensitivity than in adult hearts. If this depends upon a "fetal" cardiac sodium channel isoform, then drugs can be designed and tested for their specific action on the appropriate isoform. "Fetal" TTX-R sodium channels (like those in newborn skeletal muscle) are also expressed upon denervation and injury of adult skeletal muscle. Redfern, P., et al., *Acta Physiol Scand*, 82:70–78 (1971). If such "fetal" of other specialized sodium channel isoforms arise in pathophysiological conditions of heart (e.g., ischemia, hypertrophy, fibrillation, etc.), new anti-arrhythmic and cardiotonic agents may be targeted to these specific isoforms.

The foregoing illustrative examples relate to the isolation and characterization of mRNA and cDNA encoding sodium channel proteins, as well as the corresponding transcriptions and translations thereof to yield the corresponding proteins and polypeptides. While the present invention has been described in terms of specific methods and compositions, it is understood that variations and modifications will occur to those skilled in the art upon consideration of the present invention.

Numerous modifications and variations in the invention as described in the above illustrative examples are expected to occur to those skilled in the art and consequently only such limitations as appear in the appended claims should be placed thereon.

Accordingly it is intended in the appended claims to cover all such equivalent variations which come within the scope of the invention as claimed.

What is claimed is:

1. A purified and isolated DNA encoding rat cardiac sodium channel protein.

2. A purified and isolated DNA encoding human cardiac sodium channel protein.

3. The DNA according to claim 1 or 2 wherein said DNA is a cDNA.

4. The DNA according to claim 1 or 2 wherein said DNA is a genomic DNA.

5. The DNA according to claims 1 or 2 wherein said DNA is a partially or wholly synthetic DNA sequence.

6. A procaryotic or eucaryotic host cell stably transformed or transfected with DNA according to claim 1 or 2.

7. A viral or circular DNA plasmid vector comprising DNA according to claim 1 or 2.

8. A purified and isolated DNA encoding rat cardiac sodium channel protein as set out in FIG. 1.

* * * * *

UNITED STATES PATENT AND TRADEMARK OFFICE
CERTIFICATE OF CORRECTION

PATENT NO. : 5,380,836

DATED : January 10, 1995

INVENTOR(S) : Richard B. Rogart

It is certified that error appears in the above-identified patent and that said Letters Patent is hereby corrected as shown below:

therefor.  Column 1, line 7 Heading, after "OF" delete [TEE] and substitute --THE--, therefor.  Column 6, line 14, forth word delete [vital] and substitute --viral--, therefor.  Column 6, line 31, after "as" delete [pRH31] and substitute --pRH3-1--, Column 19, line 34 after "10" delete [uM] and substitute --$\mu$M--, therefor.

therefor.  Column 20, line 17 after "Rogart" delete [ROB.,] and substitute --R.B.,--, Signed and Sealed this Thirteenth Day of June, 1995

Attest:

BRUCE LEHMAN

*Attesting Officer*  *Commissioner of Patents and Trademarks*